United States Patent
Sakurai

(10) Patent No.: US 9,777,121 B2
(45) Date of Patent: Oct. 3, 2017

(54) DEFOAMING AGENT COMPOSITION

(71) Applicant: SHIN-ETSU CHEMICAL CO., LTD., Tokyo (JP)

(72) Inventor: Takato Sakurai, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/102,611

(22) PCT Filed: Oct. 23, 2014

(86) PCT No.: PCT/JP2014/078225
§ 371 (c)(1),
(2) Date: Jun. 8, 2016

(87) PCT Pub. No.: WO2015/087628
PCT Pub. Date: Jun. 18, 2015

(65) Prior Publication Data
US 2016/0311982 A1    Oct. 27, 2016

(30) Foreign Application Priority Data

Dec. 10, 2013   (JP) .................. 2013-255246
Dec. 10, 2013   (JP) .................. 2013-255247

(51) Int. Cl.
*B01D 19/04*        (2006.01)
*C08G 77/46*        (2006.01)
(Continued)

(52) U.S. Cl.
CPC ............. *C08G 77/46* (2013.01); *B01D 19/04* (2013.01); *C07F 7/184* (2013.01); *C08G 81/00* (2013.01)

(58) Field of Classification Search
None
See application file for complete search history.

(56) References Cited

U.S. PATENT DOCUMENTS 3,784,479 A    1/1974   Keil
3,865,544 A    2/1975   Keil
(Continued)

FOREIGN PATENT DOCUMENTS

GB    1204383    9/1970
GB    1 468 896  3/1977
(Continued)

OTHER PUBLICATIONS

International Search Report issued Jan. 13, 2015 in PCT/JP2014/078225 filed Oct. 23, 2014.
(Continued)

*Primary Examiner* — Robert S Loewe
(74) *Attorney, Agent, or Firm* — Oblon, McClelland, Maier & Neustadt, L.L.P.

(57) ABSTRACT

Provided are a Gemini-type alkyl-polyoxyalkylene-modified silicone suitable for use in preparing a silicone emulsion; a production method of thereof; and a defoaming agent composition containing such Gemini-type alkyl-polyoxyalkylene-modified silicone.
The Gemini-type alkyl-polyoxyalkylene-modified silicone is expressed by the following general formula (A):

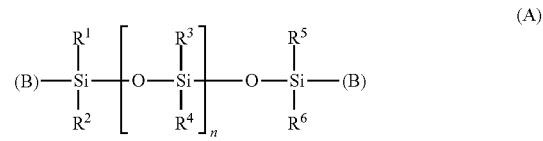

wherein each of $R^1$, $R^2$, $R^3$, $R^4$, $R^5$ and $R^6$ represents an alkyl group or the like; n represents an integer of 0 to 300; and (B)

(Continued)

represents a group expressed by the following general formula (1) or general formula (2):

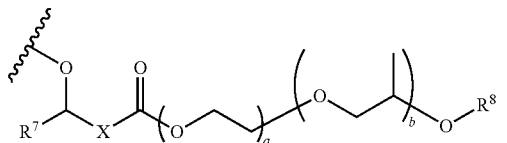

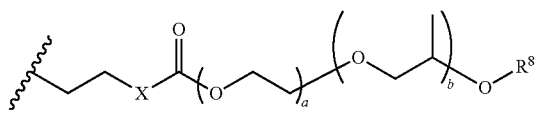

wherein each of $R^7$ and X represents a hydrocarbon group; $R^8$ represents a hydrogen atom, a hydrocarbon group, a formyl group or an acyl group; and a and b represent numbers satisfying $2 \leq a \leq 200$ and $0 \leq b \leq 200$, provided that a+b=2 to 200.

7 Claims, 6 Drawing Sheets

(51) Int. Cl.
*C08G 81/00* (2006.01)
*C07F 7/18* (2006.01)

(56) References Cited

U.S. PATENT DOCUMENTS

| | | | |
|---|---|---|---|
| 3,879,696 A | | 4/1975 | Imajyo et al. |
| 3,965,150 A | * | 6/1976 | Moeller .............. C08G 77/46 521/112 |
| 3,984,200 A | | 10/1976 | Doesburg |
| 3,984,347 A | | 10/1976 | Keil |
| 4,144,206 A | * | 3/1979 | Symeon ................ C08L 83/04 260/DIG. 16 |
| 4,150,048 A | * | 4/1979 | Schilling, Jr. ........ C08G 77/46 521/112 |
| 4,304,897 A | * | 12/1981 | Bluestein .............. C08L 83/04 525/477 |
| 4,587,320 A | * | 5/1986 | Swihart ................ A61K 8/894 528/23 |
| 6,458,453 B1 | * | 10/2002 | Hayashi ............... B82Y 30/00 106/287.1 |
| 7,084,215 B2 | * | 8/2006 | Dietz .................... A61K 8/06 525/446 |
| 2004/0122113 A1 | | 6/2004 | Zeng |
| 2004/0138087 A1 | | 7/2004 | Lyu et al. |

FOREIGN PATENT DOCUMENTS

| | | |
|---|---|---|
| JP | 49-24889 A | 3/1974 |
| JP | 49-89690 A | 8/1974 |
| JP | 51-71886 A | 6/1976 |
| JP | 51-35556 | 10/1976 |
| JP | 52-19836 | 5/1977 |
| JP | 52-22638 | 6/1977 |
| JP | 52-31836 | 8/1977 |
| JP | 53-34854 A | 3/1978 |
| JP | 54-43015 B2 | 12/1979 |
| JP | 55-23084 B2 | 6/1980 |
| JP | 7-126392 A | 5/1995 |
| JP | 9-278891 A | 10/1997 |
| JP | 2004-532720 A | 10/2004 |
| JP | 4482298 B2 | 6/2010 |

OTHER PUBLICATIONS

Notification of Reasons for Refusal issued Mar. 21, 2017 in Japanese Patent Application No. 2015-552361 (with English translation).

* cited by examiner

DEFOAMING AGENT COMPOSITION

CROSS REFERENCE TO RELEATED APPLICATIONS

This application is a 371 of International Patent Application PCT/JP2014/078225, filed on Oct. 23, 2014, and claims priority to Japanese Patent Application No. 2013-255246, filed on Dec. 10, 2013, and Japanese Patent Application No. 2013-255247, filed on Dec. 10, 2013.

TECHNICAL FILED

The present invention relates to a Gemini-type alkyl-polyoxyalkylene-modified silicone; a production method thereof; and a defoaming agent composition containing such silicone. Particularly, the present invention relates to a self-emulsifying defoaming agent composition exhibiting a favorable dispersibility in water and a superior defoaming persistence.

BACKGROUND ART (Gemini-type Alkyl-polyoxyalkylene-modified Silicone)

A conventional and mainstream surfactant has been that of a linear type composed of one hydrophilic part and one hydrophobic part. However, in recent years, developments have been made in next-generation surfactants such as those of Gemini-type or multi chain-type having multiple hydrophilic and hydrophobic parts. Further, Gemini-type surfactants having a modified structure of hydrophobic, hydrophilic and linking groups have been synthesized, and their performances have been analyzed as well.

A Gemini-type surfactant has a critical micelle concentration lower than that of a linear-type surfactant, and can help achieve a surface activity of the same level as a linear-type surfactant even when used in a very small amount. Therefore, the total amount of a surfactant used in a chemical product can be reduced in such case, and attention has thus been drawn to such Gemini-type surfactant not only as a surfactant capable of improving the productivity of a procedure where a surfactant is used, but also as an alternate environment-conscious material capable of reducing environmental burdens.

In the case of a linear-type surfactant, it is inevitable that given distances exist among the surfactant's molecules due to intermolecular repulsion. In contrast, a Gemini-type surfactant allows its linear part to be oriented close to an interface, thereby making it possible to form a dense and higher-order molecular aggregate(s). In addition, many Gemini-type surfactants are superior in properties such as emulsifying capacity, dispersibility and bubble characteristics.

In the case of a silicone oil, hydrocarbon groups and siloxane chains in a general surfactant are inferior in compatibility, which often constitutes a destabilizing factor when emulsifying the silicone oil. As a countermeasure, there may also be used in combination a silicone-type surfactant having a siloxane part. However, a problem has been that it is difficult for a silicone-type surfactant to form a solid and higher-order molecular aggregate(s) at an interface due to the amorphous nature of siloxane bonds, and that a sufficient stability cannot be ensured accordingly.

Moreover, as a silicone-type surfactant having a siloxane framework in the hydrophobic part, a surfactant having such Gemini-type structure is disclosed in Patent document 1. However, since the hydrophilic part of such surfactant is a cationic functional group, there have been limited kinds of emulsification compositions to which this surfactant can be applied.

(Self-emulsifying Defoaming Agent Composition)

As compared to other defoaming agents, a silicone-type defoaming agent has various superior properties. Thus, silicone-type defoaming agents are widely used in industrial processes associated with foam formation, such as those in the chemical industry, food industry, oil industry, textile industry, papermaking industry, paper and pulp industry or pharmaceutical industry. For example, there have been generally used an oil compound-type defoaming agent obtained by mixing a finely powdered silica with a silicone oil such as dimethylpolysiloxane, methylphenylpolysiloxane and methylvinyl polysiloxane; and an emulsion-type defoaming agent obtained by dispersing in water any of these silicone oil compounds and a surfactant. However, such emulsion-type defoaming agent bears a problem that its defoaming performance will be impaired as a result of having the emulsified particles destroyed when exposed to severe conditions such as a high-temperature condition, a highly alkalic condition and a condition where a larger shear force is applied. As an alternative to such emulsion-type defoaming agent, there have been proposed a self-emulsifying defoaming agent (Patent documents 2 to 6) employing both an organopolysiloxane modified by a polyoxyalkylene group(s) and a silicone oil compound.

However, one of the problems with such silicone-type defoaming agent is that its defoaming performance will be impaired, and separated/precipitated matters will occur, as a result of being in contact with a foam liquid, particularly an alkaline foam liquid for a long period of time.

Further, the defoaming performance thereof will deteriorate with time as compared to its initial value, if the process associated with foam formation is prolonged. In such case, extra amounts of the defoaming agent needs to be added, which may lead to various problems owing to massive addition of a defoaming agent, such as a decrease in yield.

Various proposals have been made to solve the above problems and further improve the defoaming performance. For example, there have been disclosed a method of previously hydrophobizing a silica used in an oil compound with chlorosilane or the like (Patent document 7); and a method of treating a silica with a nitrogen-containing organic silicon compound (Patent document 8). However, these inventions only provide proposals on oil compounds, and hardly discuss any approach to improve the defoaming performance through property improvement using a novel dispersing agent.

PRIOR ART DOCUMENT

Patent Document

Patent document 1: Japanese Patent No. 4482298
Patent document 2: Japanese Unexamined Patent Application Publication No. Sho 51-71886
Patent document 3: Japanese Examined Patent Application Publication No. Sho 54-43015
Patent document 4: Japanese Examined Patent Application Publication No. Sho 52-19836
Patent document 5: Japanese Examined Patent Application Publication No. Sho 52-22638
Patent document 6: Japanese Examined Patent Application Publication No. Sho 55-23084
Patent document 7: Japanese Examined Patent Application Publication No. Sho 52-31836

Patent document 8: Japanese Examined Patent Application Publication No. Sho 51-35556

SUMMARY OF THE INVENTION

Problem to be Solved by the Invention

Therefore, it is an object of the present invention to provide a novel Gemini-type alkyl-polyoxyalkylene-modified silicone suitable for use in preparing a silicone emulsion and a production method thereof; and to provide a self-emulsifying defoaming agent composition containing such Gemini-type alkyl-polyoxyalkylene-modified silicone and exhibiting a favorable water dispersibility and a superior defoaming persistence.

Means to Solve the Problem

The inventor of the present invention completed the invention as follows. That is, used as starting materials were a ricinoleic acid occupying a large part of fatty acids contained in a castor oil; and a derivative thereof, such starting materials being characterized as inexpensive and naturally derived. Further, there were performed esterifying the starting materials with a mono-endcapped polyoxyalkylene, and then condensing them with an organopolysiloxane having a reactive group at both terminals. In this way, there were obtained a Gemini-type alkyl-polyoxyalkylene-modified silicone having in one molecule three components which were a polysiloxane part, an alkyl part and a polyether part; and a production method thereof. Moreover, the inventor of the present invention found that a defoaming agent composition could exhibit a favorable water dispersibility and a superior defoaming persistence, if the composition employed, as a dispersing agent, a particular Gemini-type alkyl-polyoxyalkylene-modified silicone having in one molecule three components which were a polysiloxane part, an alkyl part and a polyether part, and contained a silicone oil compound, a polyoxyalkylene-modified organopolysiloxane and a polyoxyalkylene polymer, if necessary.

That is, the present invention is to provide the following Gemini-type alkyl-polyoxyalkylene-modified silicone; a production method thereof; and defoaming agent composition containing such Gemini-type alkyl-polyoxyalkylene-modified silicone.

<1>
A Gemini-type alkyl-polyoxyalkylene-modified silicone represented by the following general formula (A):

[Chemical formula 1]

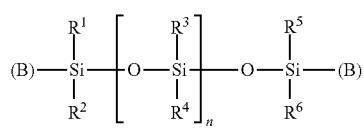

(A)

wherein $R^1$, $R^2$, $R^3$, $R^4$, $R^5$ and $R^6$ are identical to or different from one another, and each may have a halogen atom, a hydroxyl group, an amino group, a thiol group or a hydrosilyl group, representing: an alkyl group that has 1 to 30 carbon atoms; a cycloalkyl group that has 3 to 30 carbon atoms; an aryl group that has 6 to 30 carbon atoms; or an aralkyl group that has 7 to 30 carbon atoms, n represents an integer of 0 to 300, and (B) represents either an identical group or different groups expressed by the following general formula (1) or general formula (2):

[Chemical formula 2]

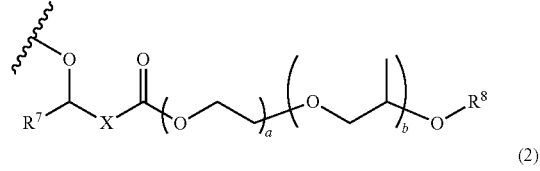

(1)

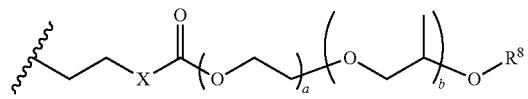

(2)

wherein each of $R^7$ and X represents a hydrocarbon group that has 1 to 40 carbon atoms and may be substituted by a halogen atom, an alkoxy group, a nitro group, a cyano group or a substituted amino group; $R^8$ represents a hydrogen atom, a hydrocarbon group having 1 to 30 carbon atoms, a formyl group or an acyl group having 2 to 30 carbon atoms; and a and b represent numbers satisfying $2 \leq a \leq 200$ and $0 \leq b \leq 200$, provided that a+b=2 to 200.

<2>
A production method of the Gemini-type alkyl-polyoxyalkylene-modified silicone as set forth in <1>, comprising:
   a first step of condensing a mono-endcapped polyoxyalkylene and a hydroxyalkyl carboxylic acid derivative by either
(a) a transesterification reaction between hydroxyl groups of the mono-endcapped polyoxyalkylene and hydroxyalkyl carboxylic acid ester, or
(b) an esterification reaction between hydroxyl groups of the mono-endcapped polyoxyalkylene and carboxyl groups of hydroxyalkyl carboxylic acid; and
   a second step of reacting a hydroxyalkyl-polyoxyalkylene condensate obtained in the first step and an organopolysiloxane having a reactive group at both terminals by either
(c) a dehydrocondensation reaction between hydroxyl groups of the hydroxyalkyl-polyoxyalkylene condensate and an organopolysiloxane having a hydrosilyl group at both terminals under the presence of a platinum group metal catalyst or a base catalyst, or
(d) a condensation reaction between hydroxyl groups of the hydroxyalkyl-polyoxyalkylene condensate and an organopolysiloxane having at both terminals a hydrolyzable group directly bonded to a silicon atom under the presence of a condensation catalyst.

<3>
A production method of the Gemini-type alkyl-polyoxyalkylene-modified silicone as set forth in <1>, comprising:
   a first step of adding a mono-endcapped polyoxyalkylene to an alkyl carboxylic acid having a double bond at main chain terminal(s) by either
(e) a transesterification reaction between hydroxyl groups of the mono-endcapped polyoxyalkylene and alkyl carboxylic acid ester having a double bond at main chain terminal(s), or
(f) an esterification reaction between hydroxyl groups of the mono-endcapped polyoxyalkylene and carboxyl groups of the alkyl carboxylic acid having a double bond at terminal(s); and a second step of subjecting an alkyl-polyoxyalkylene condensate obtained in the first step and having a double bond at terminal(s) and an organopolysiloxane having a hydrosilyl group at both terminals to an addition reaction under the presence of a platinum group metal catalyst.

<4>

The production method of the Gemini-type alkyl-polyoxyalkylene-modified silicone according to <2>, wherein the hydroxyalkyl carboxylic acid derivative is at least one selected from the group consisting of a ricinoleic acid, a 12-hydroxystearic acid, a methyl ester of the ricinoleic acid, a methyl ester of the 12-hydroxystearic acid, an ethylester of the ricinoleic acid, an ethylester of the 12-hydroxystearic acid, an n-propylester of the ricinoleic acid, an n-propylester of the 12-hydroxystearic acid, an i-propylester of the ricinoleic acid, an i-propylester of the 12-hydroxystearic acid, a butylester of the ricinoleic acid and a butylester of the 12-hydroxystearic acid.

<5>

The production method of the Gemini-type alkyl-polyoxyalkylene-modified silicone according to <3>, wherein the alkyl carboxylic acid having a double bond at terminal(s) is selected from the group consisting of an undecylenic acid, a methylester of the undecylenic acid, an ethylester of the undecylenic acid, an n-propylester of the undecylenic acid, an i-propylester of the undecylenic acid and a butylester of the undecylenic acid.

<6>

A defoaming agent composition comprising:
(A) a Gemini-type alkyl-polyoxyalkylene-modified silicone in an amount of 1 to 80% by mass and represented by the following general formula (A)

[Chemical formula 3]

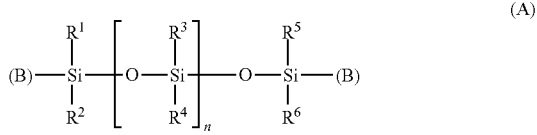

(A)

wherein $R^2$, $R^3$, $R^4$, $R^5$ and $R^6$ are identical to or different from one another, and each may have a halogen atom, a hydroxyl group, an amino group, a thiol group or a hydrosilyl group, representing: an alkyl group that has 1 to 30 carbon atoms; a cycloalkyl group that has 3 to 30 carbon atoms; an aryl group that has 6 to 30 carbon atoms; or an aralkyl group that has 7 to 30 carbon atoms, n represents an integer of 0 to 300, and (B) represents either an identical group or different groups expressed by the following general formula (1):

[Chemical formula 4]

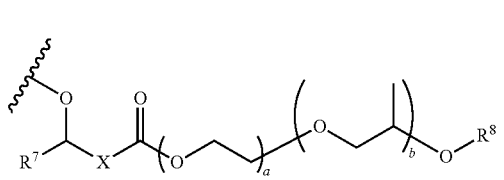

(1)

wherein each of $R^7$ and X represents a hydrocarbon group that has 1 to 40 carbon atoms and may be substituted by a halogen atom, an alkoxy group, a nitro group, a cyano group or a substituted amino group; $R^8$ represents a hydrogen atom, a hydrocarbon group having 1 to 30 carbon atoms, a formyl group or an acyl group having 2 to 30 carbon atoms; and a and b represent numbers satisfying $2 \leq a \leq 200$ and $0 \leq b \leq 200$, provided that a+b=2 to 200;

(B) a silicone oil compound in an amount of 15 to 60% by mass and containing:
  (a) an organopolysiloxane exhibiting a viscosity of 10 to 100,000 mm$^2$/s at 25° C. and represented by the following general formula (3)

$R^9{}_c SiO_{(4-c)/2}$ (3)

wherein each $R^9$ independently represents a substituted or an unsubstituted monovalent hydrocarbon group; and c represents a number of 1.9 to 2.2; and
  (b) a finely powdered silica in an amount of 0.1 to 30 parts by mass with respect to 100 parts by mass of the component (a), and exhibiting a specific surface area not smaller than 100 m$^2$/g by BET method; and
(C) at least one kind of a polyoxyalkylene-modified organopolysiloxane in an amount of 5 to 95% by mass.

<7>

The defoaming agent composition according <6>, further comprising
(D) at least one kind of a polyoxyalkylene polymer in an amount of 5 to 80% by mass.

Effects of the Invention

The Gemini-type alkyl-polyoxyalkylene-modified silicone of the present invention is suitable for use in preparing a silicone emulsion. The production method of the present invention makes it possible to produce the same through a short process and from a readily accessible fatty acid that is inexpensive and naturally derived. Further, the self-emulsifying defoaming agent composition of the present invention particularly exhibits a favorable water dispersibility and is superior in defoaming persistence.

MODE FOR CARRYING OUT THE INVENTION

Figure 1:
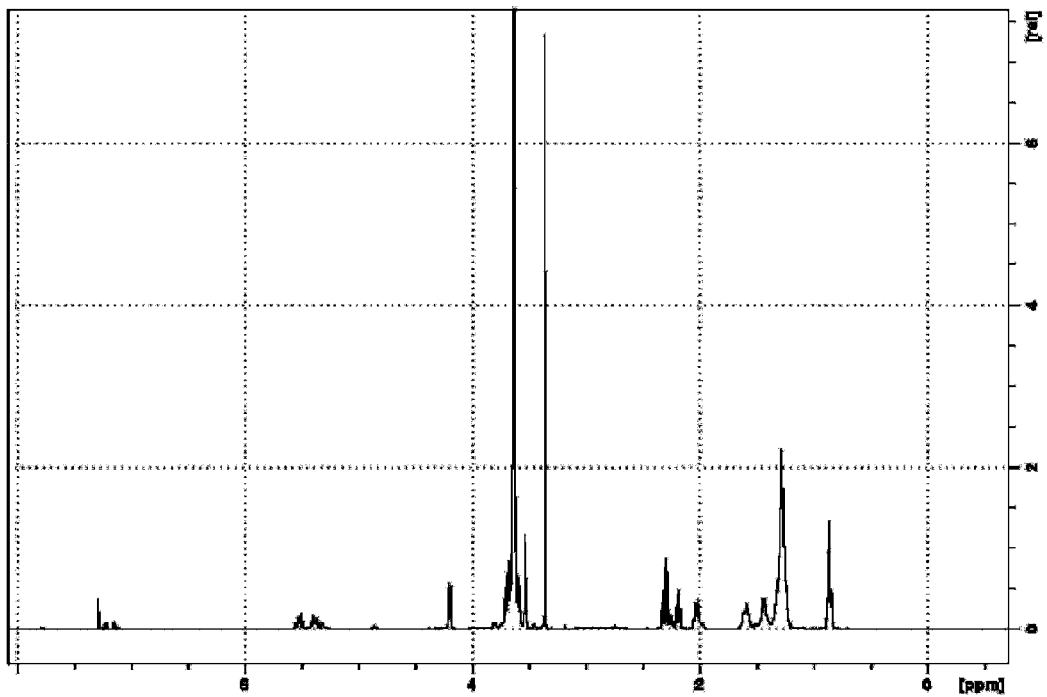
FIG. 1 is a $^1$H-NMR spectrum of a ricinoleic acid-polyoxyethylene condensate obtained in (1) of a working example 1.

Although the present invention is described in detail hereunder, the present invention is not limited to the following examples.

[Gemini-type Alkyl-polyoxyalkylene-modified Silicone]

The present invention is, for example, a Gemini-type alkyl-polyoxyalkylene-modified silicone represented by the following general formula (A), and obtained by allowing an organopolysiloxane residue having a reactive group at both terminals and an alkyl-polyoxyalkylene residue (B) to bond to each other through Si—C or Si—O bonding.

[Chemical formula 5]

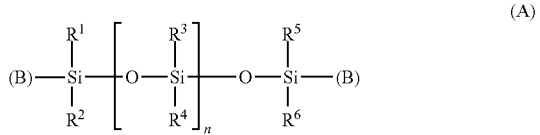

(A)

(In the above formula, R$^1$, R$^2$, R$^3$, R$^4$, R$^5$ and R$^6$ are either identical to or different from one another, each representing: an alkyl group that has 1 to 30 carbon atoms and may have a halogen atom, a hydroxyl group, an amino group, a thiol group or a hydrosilyl group; a cycloalkyl group that has 3 to 30 carbon atoms and may have a halogen atom, a hydroxyl group, an amino group, a thiol group or a hydrosilyl group; an aryl group that has 6 to 30 carbon atoms and may have a halogen atom, a hydroxyl group, an amino group, a thiol group or a hydrosilyl group; or an aralkyl group that has 7 to 30 carbon atoms and may have a halogen atom, a hydroxyl group, an amino group, a thiol group or a hydrosilyl group. n represents an integer of 0 to 300.

Those represented by (B) are either identical to or different from each other, each representing a group expressed by the following general formula (1) or a group expressed by the following general formula (2).

[Chemical formula 6]

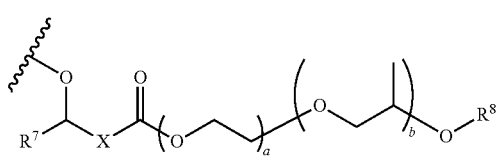

(1)

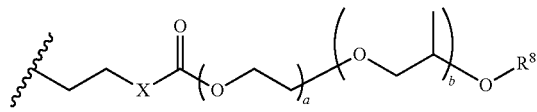

(2)

(In the above formula, each of R$^7$ and X represents a hydrocarbon group that has 1 to 40 carbon atoms and may be substituted by a halogen atom, an alkoxy group, a nitro group, a cyano group or a substituted amino group. R$^8$ represents a hydrogen atom, a hydrocarbon group having 1 to 30 carbon atoms, a formyl group or an acyl group having 2 to 30 carbon atoms. Each of a and b represents a number satisfying both 2≤a≤200 and 0≤b≤200, provided that a+b=2 to 200.))

Here, in the above general formula (A), R$^1$, R$^2$, R$^3$, R$^4$, R$^5$ and R$^6$ are either identical to or different from one another, each representing: an alkyl group that has 1 to 30 carbon atoms and may have a halogen atom, a hydroxyl group, an amino group, a thiol group or a hydrosilyl group; a cycloalkyl group that has 3 to 30 carbon atoms and may have a halogen atom, a hydroxyl group, an amino group, a thiol group or a hydrosilyl group; an aryl group that has 6 to 30 carbon atoms and may have a halogen atom, a hydroxyl group, an amino group, a thiol group or a hydrosilyl group; or an aralkyl group that has 7 to 30 carbon atoms and may have a halogen atom, a hydroxyl group, an amino group, a thiol group or a hydrosilyl group. Specific examples of these groups include an alkyl group such as a methyl group, an ethyl group, a propyl group, a butyl group, a pentyl group, a hexyl group, a heptyl group, an octyl group, a nonyl group and a decyl group; a cycloalkyl group such as a cyclopentyl group and a cyclohexyl group; an aryl group such as a phenyl group and a tolyl group; an aralkyl group such as a benzyl group and a phenethyl group; and a group whose hydrogens have been partially substituted by halogens, such as a trifluoropropyl group and a nonafluorooctyl group. Among the above groups, a methyl group is preferred.

n represents an integer of 0 to 300, preferably 2 to 100, more preferably 5 to 50. As described later about a production method of the silicone of the present invention, the above organopolysiloxane residue can be derived from, for example, an organohydrogensiloxane having an Si—H group at both terminals or an organopolysiloxane having at both terminals a hydrolyzable group bonded to a silicon atom(s).

Those represented by (B) are either identical to or different from each other, each representing a group expressed by the following general formula (1) or a group expressed by the following general formula (2).

[Chemical formula 7]

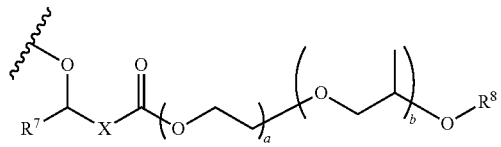

(1)

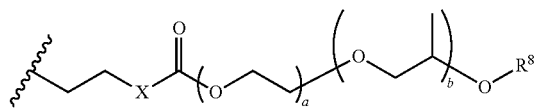
(2)

Here, each of R⁷ and X basically represents a hydrocarbon group having 1 to 40, preferably 1 to 20 carbon atoms. Particularly, examples of such hydrocarbon group include an alkyl group, an alkenylene group, a cycloalkyl group, a cycloalkenylene group, an aryl group and an arylene group. These hydrocarbon groups may also have a substituted group(s), and examples of such substituted group include an alkoxy group (e.g. methoxy group, ethoxy group, propoxy group, n-butoxy group, isobutoxy group and t-butoxy group); a halogen atom (e.g. fluorine atom and chlorine atom); a nitro group; a cyano group; and a substituted amino group (e.g. dialkylamino group). However, since each of R⁷ and X is able to be derived from an easily available material(s) and restrict side reactions, an unsubstituted linear hydrocarbon group is preferable.

R⁸ represents a hydrogen atom; an alkyl group having 1 to 30 carbon atoms, such as a methyl group, an ethyl group, a propyl group, a butyl group, a pentyl group and a hexyl group; or an acyl group having 2 to 30 carbon atoms, such as a formyl group and an acetyl group. Particularly, a methyl group, a butyl group and an acetyl group are preferred due to the ease of their availability.

a and b are integers satisfying 2≤a≤200, preferably 5≤a≤100; and 0≤b≤200, preferably 0≤b≤100, provided that a+b=2 to 200, preferably 5 to 100. Particularly, when the polyoxyalkylene portion in the above general formulae (1) and (2) includes both an ethylene oxide unit and a propylene oxide unit, the polyoxyalkylene portion may employ any of a block polymer and a random polymer of these units.

The hydroxyalkyl carboxylic acid residues in the alkyl-polyoxyalkylene residue (B) may be identical to or different from one another. Preferable examples of such hydroxyalkyl carboxylic acid include a glycolic acid; a lactic acid; a 5-hydroxyvaleric acid; a 6-hydroxycaproic acid; a ricinoleic acid; a 12-hydroxystearic acid; a 12-hydroxydodecanoic acid; a 5-hydroxydodecanoic acid; a 5-hydroxydecanoic acid; and a 4-hydroxydecanoic acid and a derivative thereof. Particularly, in terms of cost and accessibility, a ricinoleic acid and a derivative thereof; or a 12-hydroxystearic acid and a derivative thereof are preferred.

The inventor of the present invention found the following methods as a production method of the Gemini-type alkyl-polyoxyalkylene-modified silicone of the present invention.

A production method (1) of the Gemini-type alkyl-polyoxyalkylene-modified silicone has two steps.

A first step is to condense a mono-endcapped polyoxyalkylene and a hydroxyalkyl carboxylic acid derivative by either
(a) a transesterification reaction between hydroxyl groups of the mono-endcapped polyoxyalkylene and hydroxyalkyl carboxylic acid ester; or
(b) an esterification reaction between hydroxyl groups of the mono-endcapped polyoxyalkylene and carboxyl groups of hydroxyalkyl carboxylic acid.

A second step is to react a hydroxyalkyl-polyoxyalkylene condensate obtained in the first step and an organopolysiloxane having a reactive group at both terminals by either (c) a dehydrocondensation reaction between hydroxyl groups of such hydroxyalkyl-polyoxyalkylene condensate and an organopolysiloxane having a hydrosilyl group at both terminals under the presence of a platinum group metal catalyst or a base catalyst; or
(d) a condensation reaction between hydroxyl groups of such hydroxyalkyl-polyoxyalkylene condensate and an organopolysiloxane having at both terminals a hydrolyzable group directly bonded to a silicon atom under the presence of a condensation catalyst.

A production method (2) of the Gemini-type alkyl-polyoxyalkylene-modified silicone has two steps.

A first step is to add a mono-endcapped polyoxyalkylene to an alkyl carboxylic acid having a double bond at main chain terminal(s) by either
(e) a transesterification reaction between hydroxyl groups of the mono-endcapped polyoxyalkylene and alkyl carboxylic acid ester having a double bond at main chain terminal(s); or
(f) an esterification reaction between hydroxyl groups of the mono-endcapped polyoxyalkylene and carboxyl groups of the alkyl carboxylic acid having a double bond at main chain terminal(s).

A second step is to additively react an alkyl-polyoxyalkylene condensate obtained in the first step and having a double bond at terminal(s) with an organopolysiloxane having a hydrosilyl group at both terminals under the presence of a platinum group metal catalyst.

As for the condensation reaction in the first steps, the reaction conditions thereof are described in greater detail hereunder. Industrially, a type of esterification employing a direct dehydration method using an acid catalyst is desired due to the fact that such a type of esterification only yields water as a by-product and allows an easy purification.

<1. Transesterification>

Examples of a carboxylic acid used in condensing a mono-endcapped polyoxyalkylene and a hydroxyalkyl carboxylic acid ester or an alkyl carboxylic acid ester having a double bond at its main chain terminal(s) through a transesterification reaction, include a glycolic acid, a lactic acid, a 5-hydroxyvaleric acid, a 6-hydroxycaproic acid, a ricinoleic acid, a 12-hydroxystearic acid, a 12-hydroxydodecanoic acid, a 5-hydroxydodecanoic acid, a 5-hydroxydecanoic acid, a 4-hydroxydecanoic acid, a methyl ester of an undecylenic acid, an ethylester of an undecylenic acid, an n-propylester of an undecylenic acid, an i-propylester of an undecylenic acid and a butylester of an undecylenic acid. Particularly, in terms of cost and accessibility, a ricinoleic acid, a 12-hydroxystearic acid, and a methyl ester and an ethylester of an undecylenic acid are preferred.

It is preferred that the hydroxyalkyl carboxylic acid ester or the alkyl carboxylic acid ester having a double bond at its main chain terminal(s) be used in an amount of 0.9 to 1.4 mol, more preferably 1.0 to 1.3 mol, particularly preferably 1.05 to 1.25 mol, with respect to 1 mol of the mono-endcapped polyoxyalkylene.

There are no particular restrictions on a method of adding the hydroxyalkyl carboxylic acid ester or the alkyl carboxylic acid ester having a double bond at its main chain terminal(s). In fact, a total amount thereof may be added to the mono-endcapped polyoxyalkylene at the time of preparation to effect the reactions; or they may be added in parts during the course of the reactions.

The reactions may be effected either with or without a solvent. If using a solvent, while there are no particular restrictions on the solvent to be used, preferable examples of such solvent include an aromatic hydrocarbon solvent such as toluene and xylene; an aliphatic hydrocarbon solvent such as hexane and heptane; an ether type solvent such as diethyl ether, tetrahydrofuran, monoethylene glycol dimethylether and diethylene glycol dimethylether; a ketone type solvent such as acetone, methylethyl ketone and methyl isobutyl ketone; an ester type solvent such as ethyl acetate, butyl acetate and gamma butyrolactone; and an amide type solvent such as dimethyl formamide, dimethyl acetamide and N-methyl pyrolidone. Each of these solvents may be used singularly, or an arbitrary number of these solvents may be used in a mixed manner.

If using such solvent, it is used in an amount at which the concentration of the hydroxyalkyl carboxylic acid ester or the alkyl carboxylic acid ester having a double bond at its main chain terminal(s), each as a raw material, exhibits a lower limit of not lower than 0.1% by mass in general, preferably not lower than 1% by mass; and an upper limit, though not restricted, of not higher than 80% by mass in general, preferably not higher than 60% by mass.

A transesterification reaction is usually performed under the presence of a catalyst(s). Usable catalysts include those that can be used in performing transesterification reactions. Examples of such catalysts include a transition metal compound such as titanium tetraisopropoxide; an alcoholate of an alkali or alkali earth metal, such as sodium methoxide; an alkoxide of aluminum, such as aluminum triisopropoxide; a hydroxide of an alkali or alkali earth metal, such as lithium hydroxide and sodium hydroxide; and a tin compound such as dibutyltin oxide and dioctyltin oxide.

These catalysts are used in a minimum amount of not smaller than 0.01 mol % in general, preferably not smaller than 0.1 mol %, more preferably not smaller than 0.5 mol %; and a maximum amount of not larger than 50 mol % in general, preferably not larger than 20 mol %, more preferably not larger than 10 mol %, with respect to 1 mol of the hydroxyalkyl carboxylic acid ester or the alkyl carboxylic acid ester having a double bond at its main chain terminal(s), each as a raw material.

There are no particular restrictions on a method of adding these catalysts. The reaction with the mono-endcapped polyoxyalkylene may be performed after a total amount of the catalysts has been added to the hydroxyalkyl carboxylic acid ester or the alkyl carboxylic acid ester having a double bond at its main chain terminal(s), each as a raw material. Further, the reaction with the hydroxyalkyl carboxylic acid ester or the alkyl carboxylic acid ester having a double bond at its main chain terminal(s) may be performed after the total amount of the catalyst(s) has been added to the mono-endcapped polyoxyalkylene at the time of preparing the mono-endcapped polyoxyalkylene. Furthermore, the hydroxyalkyl carboxylic acid ester or the alkyl carboxylic acid ester having a double bond at its main chain terminal(s); and the mono-endcapped polyoxyalkylene may be previously mixed together, followed by adding the total amount of the catalysts thereto to effect the reactions. Also, there may be employed a method where the catalysts are added in parts during the course of the reactions.

It is preferred that the reactions be performed using a reactor equipped with a normal stirring device. Further, the reactions may be performed while distilling away the alcohols generated during the course of the reactions, and shifting the equilibrium so as to favor the product system.

As for a reaction temperature, it is preferred that heating be performed to achieve a sufficient reaction rate. Specifically, it is performed at a minimum temperature of not lower than −10° C. in general, preferably not lower than 0° C.; and a maximum temperature of not higher than 200° C. in general, preferably not higher than 150° C.

A reaction time may be arbitrarily determined. Particularly, since alcohols are generated as the reactions proceed, it is preferred that the reactions be performed continuously until a given amount of alcohols has been obtained. As for a normal reaction time, a lower limit thereof is not less than 10 min in general, preferably not less than 30 min. While there are no particular restrictions on an upper limit of such reaction time, the upper limit is not more than 50 hours in general, preferably not more than 30 hours.

<2. Direct Dehydration Method>

Examples of a carboxylic acid used in condensing the mono-endcapped polyoxyalkylene and the hydroxyalkyl carboxylic acid or the alkyl carboxylic acid having a double bond at its main chain terminal(s) through a direct dehydration method, include glycolic acid; a lactic acid; a 5-hydroxyvaleric acid; a 6-hydroxycaproic acid; a ricinoleic acid; a 12-hydroxystearic acid; a 12-hydroxydodecanoic acid; a 5-hydroxydodecanoic acid; a 5-hydroxydecanoic acid; a 4-hydroxydecanoic acid; and a undecylenic acid. Particularly, in terms of cost and accessibility, a ricinoleic acid, a 12-hydroxystearic acid and an undecylenic acid are preferred.

The hydroxyalkyl carboxylic acid or the alkyl carboxylic acid having a double bond at its main chain terminal(s) is used in a minimum amount of not smaller than 0.9 molar equivalents, preferably not smaller than 1.0 molar equivalents, more preferably not smaller than 1.05 molar equivalents, and a maximum amount of not larger than 1.4 molar equivalents, preferably not larger than 1.3 molar equivalents, more preferably not larger than 1.25 molar equivalents, with respect to the molar number of the mono-endcapped polyoxyalkylene.

There are no particular restrictions on a method of adding such hydroxyalkyl carboxylic acid or the alkyl carboxylic acid having a double bond at its main chain terminal(s). In fact, a total amount thereof may be added to the mono-endcapped polyoxyalkylene at the time of preparation to effect the reactions; or they may be added in parts during the course of the reactions.

When esterifying the mono-endcapped polyoxyalkylene and the hydroxyalkyl carboxylic acid or the alkyl carboxylic acid having a double bond at its main chain terminal(s), the reactions shall proceed rapidly under the presence of a dehydration condensation agent. There are no particular restrictions on such condensation agent, as long as it is a widely known condensation agent for performing esterification. Particularly, preferable examples of such condensation agent include N,N'-dicyclohexylcarbodiimide, 2-chloro-1,3-dimethylimidazolium chloride and a propane-phosphonic anhydride. Moreover, at that time, there may also be used in combination basic organic materials such as pyridine, 4-dimethylaminopyridine and triethylamine. As for a reaction temperature normally employed in such reaction, an lower limit thereof is −20° C. in general, preferably −10° C.; and an upper limit thereof is 150° C. in general, preferably 100° C.

Theoretically, it is sufficient if the dehydration condensation agent is used in an amount equivalent to or greater than that of the hydroxyalkyl carboxylic acid or the alkyl carboxylic acid having a double bond at its main chain terminal(s). Particularly, the dehydration condensation agent may also be used in an excessive amount. It is preferred that such dehydration condensation agent be used in an amount of not smaller than 1.0 molar equivalent, more preferably not smaller than 1.1 molar equivalents.

Even when the dehydration condensation agent is not used, the mono-endcapped polyoxyalkylene and the hydroxyalkyl carboxylic acid or the alkyl carboxylic acid having a double bond at its main chain terminal(s) can still be reacted under the presence of an acid while distilling away the water generated.

There are no particular restrictions on the acid used here, as long as it is an acid normally used in performing esterification reaction. Examples of such acid include an inorganic acid such as sulfuric acid and hydrochloric acid; an organic sulfonic acid such as p-toluenesulfonic acid, methanesulfonic acid and camphorsulfonic acid; a Lewis acid such as an acid type ion-exchange resin and a boron fluoride-ether complex; and a water-soluble Lewis acid such as lanthanide triflate. Each of these acids may be used singularly, or any two or more of them may be used in a mixed manner. Preferred is p-toluenesulfonic acid.

Such acid(s) are used in a minimum amount of not smaller than 0.001 mol %, preferably not smaller than 0.01 mol %, more preferably not smaller than 0.1 mol %, with respect to 1 mol of the hydroxyalkyl carboxylic acid or the alkyl carboxylic acid having a double bond at its main chain terminal(s). Meanwhile, there is no upper limit on the amount of the acid(s) used. The acid(s) are used in an amount of not larger than 10 molar equivalents, preferably not larger than 1 molar equivalent.

There are no particular restrictions on a method of adding such dehydration condensation agent or acid(s). In fact, the reaction with the mono-endcapped polyoxyalkylene may be performed after a total amount of such dehydration condensation agent or acid(s) has been added to the hydroxyalkyl carboxylic acid or the alkyl carboxylic acid having a double bond at its main chain terminal(s), each as a raw material. Further, the reaction with the hydroxyalkyl carboxylic acid or the alkyl carboxylic acid having a double bond at its main chain terminal(s) may be performed after adding the total amount of such dehydration condensation agent or acid(s) at the time of preparing the mono-endcapped polyoxyalkylene. Furthermore, the alkyl carboxylic acid having a double bond at its main chain terminal(s) and the mono-endcapped polyoxyalkylene may be previously mixed together, followed by adding the total amount of such dehydration condensation agent or acid(s) thereto to effect the reactions. Also, the dehydration condensation agent or acid(s) may even be added in parts during the course of the reactions.

Such reactions may be performed either with or without a solvent. If using a solvent, while there are no particular restrictions on the solvent to be used, preferable examples of such solvent include an aromatic hydrocarbon solvent such as toluene and xylene; an aliphatic hydrocarbon solvent such as hexane and heptane; an ether type solvent such as diethyl ether, tetrahydrofuran, monoethylene glycol dimethylether and diethylene glycol dimethylether; and a halogen type solvent such as methylene chloride, chloroform and carbon tetrachloride. Each of these solvents may be used singularly, or an arbitrary number of these solvents may be used in a mixed manner. If the reactions are to be performed while distilling away the water generated under the presence of an acid catalyst without using a dehydration condensation agent, it is preferred that there be used a water-insoluble solvent such as toluene and xylene in terms of dehydration efficiency.

If using a solvent, the solvent is used in an amount at which the hydroxyalkyl carboxylic acid or the alkyl carboxylic acid having a double bond at its main chain terminal(s), each as a raw material, exhibits a minimum concentration of not lower than 0.1% by mass in general, preferably not lower than 1% by mass; and a maximum concentration, though not restricted in any particular way, of not higher than 80% by mass in general, preferably not higher than 60% by mass.

The reactions are normally performed at a temperature not lower than the boiling. point of a solvent used, and are performed while distilling away the water generated.

Although a reaction time may be arbitrarily determined, the end point of a reaction can be known by measuring the amount of the water generated. A reaction time normally includes a drop time, and a lower limit of such reaction time is not less than 10 min in general, preferably not less than 30 min. While there are no particular restrictions on an upper limit of such reaction time, the upper limit of such reaction time is not more than 20 hours in general, preferably not more than 10 hours.

Described in greater detail hereunder are the reaction conditions for the condensation reaction with the organopolysiloxane in the second step.

<1. Dehydrocondensation>

In order to introduce an organopolysiloxane group into the hydroxyalkyl-polyoxyalkylene condensate obtained in the first step, the hydroxyalkyl-polyoxyalkylene condensate is subject to dehydrocondensation with an organopolysiloxane having hydrogen atoms bonded to silicon atoms (i.e. Si—H groups) and having a hydrosilyl group at both terminals under the presence of a platinum group metal catalyst such as platinum or rhodium or under the presence of a base catalyst.

It is preferred that the organopolysiloxane having a hydrosilyl group at both terminals be used in an amount of 0.4 to 0.55 mol, particularly preferably 0.45 to 0.52 mol, with respect to 1 mol of the hydroxyalkyl-polyoxyalkylene condensate.

There are no particular restrictions on a method of adding such organopolysiloxane having a hydrosilyl group at both terminals. In fact, a total amount of such organopolysiloxane may be added to the hydroxyalkyl-polyoxyalkylene condensate at the time of preparation to effect the reactions. Further, the organopolysiloxane may also be added in parts during the course of the reactions. Particularly, it is preferred that such organopolysiloxane be added by drops using a dropping funnel or the like to avoid a rapid hydrogen gas generation and release of heat.

A platinum catalyst is preferred as a platinum group metal catalyst used in performing the above dehydrocondensation reaction. Examples of such platinum catalyst include a chloroplatinic acid, an alcohol-modified chloroplatinic acid and a chloroplatinic acid-vinylsiloxane complex. Further, examples of a base catalyst include alkyl amines such as monomethylamine, dimethylamine, monoethylamine, diethylamine, diethylhydroxylamine, triethylamine, triethanolamine, monopropylamine, dipropylamine, dipropylhydroxylamine, tripropylamine, monobutylamine, dibutylamine, dibutylhydroxylamine, tributylamine, monoheptylamine, monohexylamine, dihexylamine, dihexyihydroxylamine, trihexylamine, monooctylamine, dioctylamine, dioctylhydroxylamine, trio ctylamine, monolaurylamine, dilaurylamine, dilaurylhydroxylamine, trilaurylamine, monostearylamine, distearylamine, distearyl hydroxylamine, monooleylamine, dioleylamine, dioleylhydroxylamine and trioleylamine.

The amount of such dehydrocondensation reaction catalyst used may simply be an effective amount, and there are no particular restrictions on the amount of such dehydrocondensation reaction catalyst used. Particularly, it is preferred that such catalyst be used in an amount where the amount of a platinum group metal such as platinum or rhodium becomes not larger than 50 ppm in general, particularly preferably not larger than 20 ppm, and exhibits a lower limit value of not smaller than 0.1 ppm, on a mass basis with respect to a total amount of the organopolysiloxane having a hydrosilyl group at both terminals and the hydroxyalkyl-polyoxyalkylene condensate. Further, there are likewise no particular restrictions on the amount of the base catalyst used. Particularly, it is preferred that such base catalyst be used in an amount of not larger than 2% by mass in general, particularly preferably not larger than 1% by mass, and in a minimum amount of not smaller than 0.01% by mass, on a mass basis with respect to a total amount of the organopolysiloxane having a hydrosilyl group at both terminals and the hydroxyalkyl-polyoxyalkylene condensate.

There are no particular restrictions on a method of adding these dehydrocondensation reaction catalysts. The reaction with the hydroxyalkyl-polyoxyalkylene condensate may be performed after adding a total amount of such catalysts to the organopolysiloxane as a raw material having a hydrosilyl group at both terminals. Further, the reaction with the organopolysiloxane having a hydrosilyl group at both terminals may be performed after adding the total amount of such catalysts at the time of preparing the hydroxyalkyl-polyoxyalkylene condensate. Furthermore, the organopolysiloxane having a hydrosilyl group at both terminals and the hydroxyalkyl-polyoxyalkylene condensate may be previously mixed together, followed by adding the total amount of such catalysts thereto to effect the reactions. Also, there may be employed a method where the catalysts are added in parts during the course of the reactions.

Moreover, the above dehydrocondensation reaction may also be performed in an organic solvent if necessary. As such organic solvent, those without active hydrogens are desired. Examples of such organic solvent include an aromatic hydrocarbon such as toluene and xylene; an aliphatic or alicyclic hydrocarbon such as n-pentane, n-hexane and cyclohexane; and a halogenated hydrocarbon such as dichloromethane, chloroform and carbon tetrachloride.

Such solvent is used in an amount at which the concentration of the hydroxyalkyl-polyoxyalkylene condensate as a raw material exhibits a lower limit value of not lower than 0.1% by mass in general, preferably not lower than 1% by mass; and an upper limit value, though not restricted in any particular way, of not higher than 80% by mass in general, preferably not higher than 60% by mass.

Although there are no particular restrictions on the conditions for the dehydrocondensation reaction, it is desired that the reaction be performed for about 1 to 10 hours under reflux.

<2. Condensation with Organopolysiloxane Having Hydrolyzable Group at Both Terminals>

In order to introduce an organopolysiloxane group into the hydroxyalkyl-polyoxyalkylene condensate obtained in the first step, the hydroxyalkyl-polyoxyalkylene condensate is subject to a condensation reaction with an organopolysiloxane having at both terminals a hydrolyzable group bonded to a silicon atom(s) under the presence of a condensation catalyst.

Here, examples of the above hydrolyzable group include those having an alkoxy group directly bonded to a silicon atom(s), such as a methoxy group, an ethoxy group, a propoxy group, a butoxy group, a methoxyethoxy group and an isopropenoxy group; an acyloxy group such as an acetoxy group; an amino group such as an ethylamino group; an oxime group such as an amide group and an ethylmethyl butanoxime group; and/or halogen atoms such as an chlorine atom and a bromine atom. Particularly, a methoxy group, an ethoxy group, a propoxy group and a butoxy group are industrially favorable.

In addition, a part of such alkoxy group may be substituted by groups such as $CH_3COO-$, $CH_3(C_2H_5)C=NO-$, $(C_2H_5)_2N-$, $CH_3CO(C_2H_5)N-$ and $CH_2=(CH_3)CO-$.

It is preferred that the organopolysiloxane having at both terminals a hydrolyzable group bonded to a silicon atom(s) be used in an amount of 0.4 to 0.55 mol, more preferably 0.45 to 0.52 mol, with respect to 1 mol of the hydroxyalkyl-polyoxyalkylene condensate.

There are no particular restrictions on a method of adding such organopolysiloxane having at both terminals a hydrolyzable group bonded to a silicon atom(s). A total amount thereof may be added to the hydroxyalkyl-polyoxyalkylene condensate at the time of preparation to effect the reactions. Further, such organopolysiloxane may also be added in parts during the course of the reactions.

Examples of the condensation catalyst used in the above reactions include an organic tin compound (e.g. dimethyltin dimethoxide, dioctyltin dimethoxide and dibutyltin dilaurate), an organic titanium compound (e.g. tetra n-butyltitanate), an organic acid (e.g. acetic acid, methanesulfonic acid and fluorine-modified carboxylic acid) and an inorganic acid (e.g. hydrochloric acid and sulfuric acid). Among these catalysts, acetic acid, tetra n-butyltitanate, dibutyltin dilaurate, fluorine-modified carboxylic acid and the like are particularly favorable.

The amount of the condensation catalyst added may simply be the so-called catalyst amount. Normally, such condensation catalyst is added in an amount of 0.01 to 5 parts by mass, particularly preferably 0.1 to 1 parts by mass, with respect to 100 parts by mass of a total of the hydroxyalkyl-polyoxyalkylene condensate and the organopolysiloxane having a hydrolyzable group at both terminals.

There are no particular restrictions on a method of adding these dehydrocondensation reaction catalysts. The reaction with the hydroxyalkyl-polyoxyalkylene condensate may be performed after adding a total amount of such dehydrocondensation reaction catalysts to the organopolysiloxane as a raw material having a hydrolyzable group at both terminals. Further, the reaction with the organopolysiloxane having a hydrolyzable group at both terminals may be performed after adding the total amount of such dehydrocondensation reaction catalysts at the time of preparing the hydroxyalkyl-polyoxyalkylene condensate. Furthermore, the organopolysiloxane having a hydrolyzable group at both terminals and the hydroxyalkyl-polyoxyalkylene condensate may be previously mixed together, followed by the adding the total amount of such dehydrocondensation reaction catalysts thereto to effect the reactions. Also, the dehydrocondensation reaction catalysts may also be added in parts during the course of the reactions.

Further, although there are no particular restrictions on a solvent used in performing the above condensation reaction, favorable examples of such solvent include an aromatic hydrocarbon solvent such as toluene and xylene; an aliphatic hydrocarbon solvent such as hexane and heptane; an ether type solvent such as diethyl ether, tetrahydrofuran, monoethylene glycol dimethylether and diethylene glycol dimethylether; a ketone type solvent such as acetone, methylethyl ketone and methylisobutyl ketone; an ester type solvent such as ethyl acetate, butyl acetate and gamma-butyrolactone; and an amide type solvent such as dimethyl formamide, dimethyl acetamide and N-methyl pyrrolidone.

Each of these solvents may be used singularly, or an arbitrary number of these solvents may be used in a mixed manner.

These solvents are used in an amount at which the concentration of the hydroxyalkyl-polyoxyalkylene condensate as a raw material exhibits a lower limit value of not lower than 0.1% by mass in general, preferably not lower than 1% by mass; and an upper limit value, though not restricted in any particular way, of not higher than 80% by mass in general, preferably not higher than 60% by mass.

Although there are no particular restrictions on the reaction conditions, it is desired that the reactions be performed at a temperature not lower than the boiling point of the solvent(s) used, and that solvent displacement be repeatedly performed several times so as to remove the hydrolyzable group-derived components generated and shift the equilibrium so as to favor the product system while the reactions are taking place.

<3. Addition Reaction with Both-Terminated Organohydrogenpolysiloxane>

In order to introduce an organopolysiloxane group into the alkyl-polyoxyalkylene condensate obtained in the first step and having a double bond at its terminal(s), there is employed a method where an addition reaction with the organopolysiloxane having a hydrosilyl group at both terminals is performed under the presence of a platinum group metal catalyst such as platinum or rhodium.

It is preferred that the organopolysiloxane having a hydrosilyl group at both terminals be used in an amount of 0.4 to 0.55 mol, more preferably 0.45 to 0.52 mol, with respect to 1 mol of the alkyl-polyoxyalkylene condensate having a double bond at its terminal(s).

There are no particular restrictions on a method of adding such organopolysiloxane having a hydrosilyl group at both terminals. In fact, a total amount thereof may be added to the alkyl-polyoxyalkylene condensate having a double bond at its terminal(s) at the time of preparation to effect the reactions. Further, the organopolysiloxane having a hydrosilyl group at both terminals may also be added in parts during the course of the reactions. However, it is desired that such organopolysiloxane having a hydrosilyl group at both terminals be added by drops using a dropping funnel or the like to avoid the release of heat due to a rapid reaction.

A platinum catalyst is preferred as a platinum group metal catalyst used in performing the above addition reaction. Examples of such platinum catalyst include a chloroplatinic acid, an alcohol-modified chloroplatinic acid and a chloroplatinic acid-vinylsiloxane complex.

Here, there are no particular restrictions on the amount of such addition reaction catalyst used. In fact, an effective amount thereof is sufficient. Particularly, it is preferred that such catalyst be used in an amount where the amount of a platinum group metal such as platinum or rhodium becomes not larger than 50 ppm in general, particularly preferably not larger than 20 ppm, and exhibits a lower limit value of not smaller than 0.1 ppm, on a mass basis with respect to a total amount of the organopolysiloxane having a hydrosilyl group at both terminals and the alkyl-polyoxyalkylene condensate.

Further, there are likewise no particular restrictions on the amount of alkylamine used. Particularly, it is preferred that alkylamine be used in an amount of not larger than 2% by mass in general, particularly preferably not larger than 1% by mass, and in a minimum amount of not smaller than 0.01% by mass, on a mass basis with respect to a total amount of the organopolysiloxane having a hydrosilyl group at both terminals and the alkyl-polyoxyalkylene condensate.

There are no particular restrictions on a method of adding these addition reaction catalysts. In fact, the reaction with the alkyl-polyoxyalkylene condensate having a double bond at its terminal(s) may be performed after adding a total amount of such addition reaction catalysts to the organopolysiloxane as a raw material having a hydrosilyl group at both terminals. Further, the reaction with the organopolysiloxane having a hydrosilyl group at both terminals may be performed after adding the total amount of such addition reaction catalysts at the time of preparing the alkyl-polyoxyalkylene condensate having a double bond at its terminal(s). Furthermore, the organopolysiloxane having a hydrosilyl group at both terminals and the alkyl-polyoxyalkylene condensate having a double bond at its terminal(s) may be previously mixed together, followed by adding the total amount of such addition reaction catalysts thereto to effect the reactions. Also, the addition reaction catalysts may be added in parts during the course of the reactions.

The above addition reaction may also be performed in an organic solvent if necessary. As such organic solvent, those without active hydrogens are desired. Examples of such organic solvent include an aromatic hydrocarbon such as toluene and xylene; an aliphatic or alicyclic hydrocarbon such as n-pentane, n-hexane and cyclohexane; and a halogenated hydrocarbon such as dichloromethane, chloroform and carbon tetrachloride.

Such solvent is used in an amount at which the concentration of the alkyl-polyoxyalkylene condensate having a double bond at its terminal(s) exhibits a lower limit value of not lower than 0.1% by mass in general, preferably not lower than 1% by mass; and an upper limit value, though not restricted in any particular way, of not higher than 80% by mass in general, preferably not higher than 60% by mass.

Although there are no particular restrictions on the conditions of the above addition reaction, it is preferred that the addition reaction be performed for about 1 to 10 hours under reflux.

[Defoaming Agent Composition]

<(A) Gemini-Type Alkyl-Polyoxyalkylene-Modified Silicone>

The component (A) of a defoaming agent composition of the present invention is the aforementioned Gemini-type alkyl-polyoxyalkylene-modified silicone represented by the following general formula (A), and obtained by allowing an organopolysiloxane residue and an alkyl-polyoxyalkylene residue (1) to bond to each other through Si—O bonding. The component (A) is to assist the dispersion of a silicone oil compound of the composition of the present invention, and impart a favorable water dispersibility and a favorable defoaming persistence. Such component (A) may be used singularly, or two or more kinds thereof may be used in combination.

[Chemical formula 8]

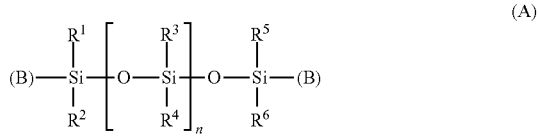

(A)

(In the above formula, $R^1$, $R^2$, $R^3$, $R^4$, $R^5$ and $R^6$ are either identical to or different from one another, each representing: an alkyl group that has 1 to 30 carbon atoms and may have a halogen atom, a hydroxyl group, an amino group, a thiol group or a hydrosilyl group; a cycloalkyl group that has 3 to 30 carbon atoms and may have a halogen atom, a hydroxyl group, an amino group, a thiol group or a hydrosilyl group; an aryl group that has 6 to 30 carbon atoms and may have a halogen atom, a hydroxyl group, an amino group, a thiol group or a hydrosilyl group; or an aralkyl group that has 7 to 30 carbon atoms and may have a halogen atom, a hydroxyl group, an amino group, a thiol group or a hydrosilyl group. n represents an integer of 0 to 300.

Those represented by (B) are either identical to or different from each other, each representing a group expressed by the following general formula (1)

[Chemical formula 9]

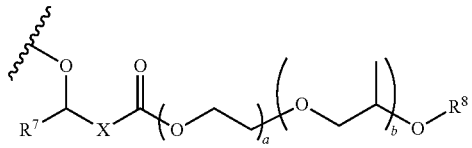

(1)

(In the above formula, each of $R^7$ and X represents a hydrocarbon group that has 1 to 40 carbon atoms and may be substituted by a halogen atom, an alkoxy group, a nitro group, a cyano group or a substituted amino group. $R^8$ represents a hydrogen atom, a hydrocarbon group having 1 to 30 carbon atoms, a formyl group or an acyl group having 2 to 30 carbon atoms. Each of a and b represents a number satisfying both $2 \leq a \leq 200$ and $0 \leq b \leq 200$, provided that a+b=2 to 200.))

In terms of defoaming performance, dispersibility and workability, the Gemini-type alkyl-polyoxyalkylene-modified silicone (A) has a viscosity of 50 to 100,000 mm²/s, preferably 100 to 20,000 mm²/s when measured by a Cannon-Fenske viscometer (SO) at 25° C. A viscosity lower than 50 mm²/s leads to an inferior defoaming performance and an inferior dispersibility. Meanwhile, a viscosity higher than 100,000 mm²/s causes the viscosity of the defoaming agent composition to increase such that an unfavorable workability will be resulted.

Following are specific examples of the Gemini-type alkyl-polyoxyalkylene-modified silicone (A).

[Chemical formula 10]

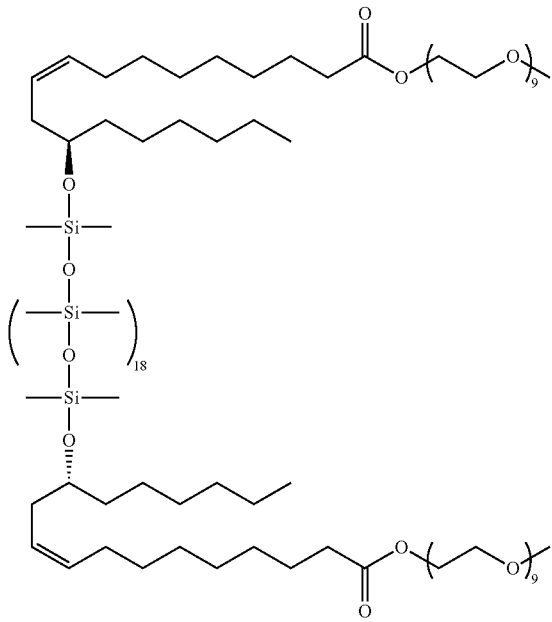

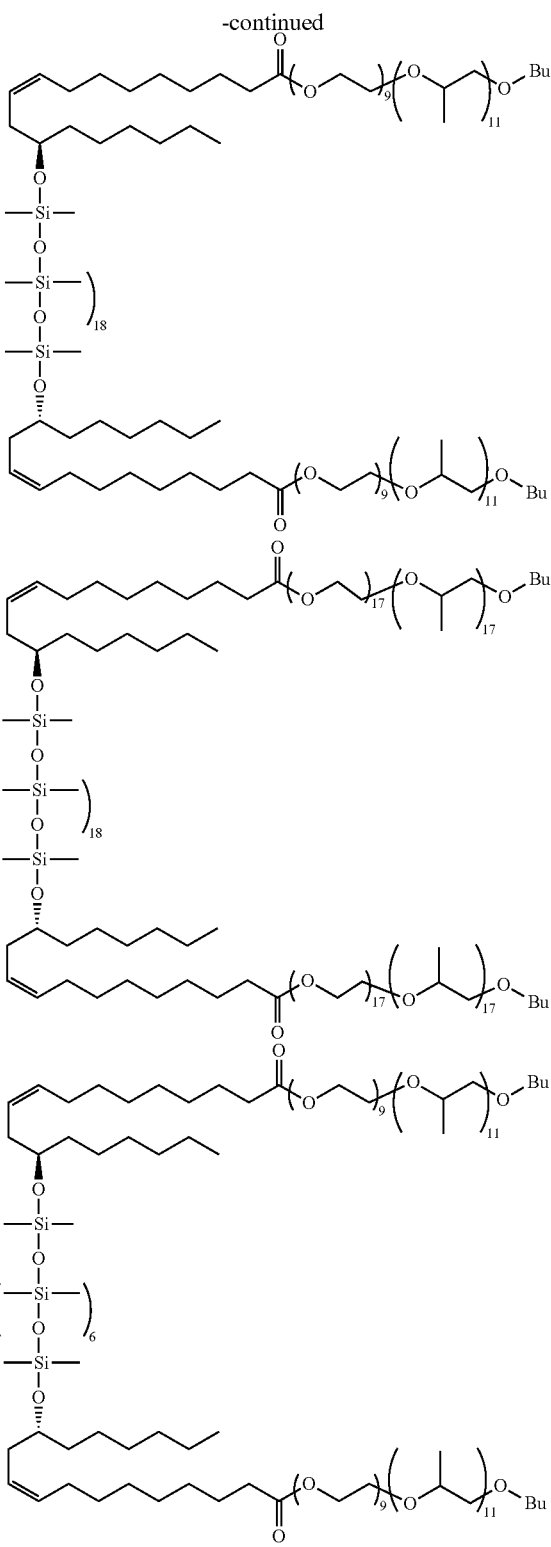

In the defoaming agent composition of the present invention, the Gemini-type alkyl-polyoxyalkylene-modified silicone (A) is contained in an amount of 1 to 80% by mass, preferably 5 to 50% by mass, with respect to the whole defoaming agent composition. The defoaming performance of the composition may be impaired, if the Gemini-type alkyl-polyoxyalkylene-modified silicone (A) is contained at a ratio of greater than 80% by mass. Meanwhile, the dispersibility in an aqueous system may be impaired, if the Gemini-type alkyl-polyoxyalkylene-modified silicone (A) is contained at a ratio of lower than 1% by mass.

<(B) Silicone Oil Compound>

A silicone oil compound is a main component for imparting a defoaming property to the composition, and is comprised of an organopolysiloxane (a) and a fine powdered silica (b). Such silicone oil compound may be used singularly, or two or more kinds thereof may be used in combination.

((a) Organopolysiloxane)

An organopolysiloxane may be either linear or branched. Such organopolysiloxane may be used singularly, or two or more kinds thereof may be used in combination. This organopolysiloxane is represented by the following general formula (3):

$$R^9{}_c SiO_{(4-c)/2} \quad (3)$$

(In the above formula, each $R^9$ independently represents a substituted or an unsubstituted monovalent hydrocarbon group; and c represents a number of 1.9 to 2.2.) Here, the organopolysiloxane represented by the above general formula (3) is essentially hydrophobic.

In the general formula (3), each $R^9$ is independently and preferably a substituted or an unsubstituted monovalent hydrocarbon group having 1 to 18 carbon atoms.

Examples of such monovalent hydrocarbon group include an alkyl group such as a methyl group, an ethyl group, a propyl group, a butyl group, a pentyl group, a hexyl group, a heptyl group, an octyl group, a nonyl group, a decyl group, a dodecyl group, a tridecyl group, a tetradecyl group, a hexadecyl group and an octadecyl group; a cycloalkyl group such as a cyclohexyl group; an alkenyl group such as a vinyl group and an allyl group; an aryl group such as a phenyl group and a tolyl group; and an aralkyl group such as a styryl group and an α-methylstyryl group. Examples of such monovalent hydrocarbon group also include a chloromethyl group, a 3-chloropropyl group, a 3,3,3-trifluoropropyl group, a cyanoethyl group, a 3-aminopropyl group and a N-(β-aminoethyl)-γ-aminopropyl group that are obtained by substituting a part of or all the hydrogen atoms bonded to the carbon atoms in the aforementioned groups with, for example, a halogen atom, a cyano group, an amino group and/or a hydroxyl group. Among these groups, it is preferred, in terms of defoaming performance and economic efficiency, that a methyl group occupy not less than 80%, particularly not less than 90% of a total number of the groups represented by $R^9$. c is a number satisfying $1.9 \leq c \leq 2.2$, preferably $1.95 \leq c \leq 2.15$. The terminal(s) of such organopolysiloxane may be blocked by a triorganosilyl group represented by $R^9{}_3Si—$, or a diorganohydroxysilyl group represented by $HOR^9{}_2Si—$.

In terms of defoaming performance and workability, it is preferred that the above organopolysiloxane exhibit a viscosity of 10 to 100,000 mm²/s, more preferably 50 to 10,000 mm²/s when measured by an Ostwald viscometer at 25° C. A viscosity lower than the lower limit value will result in an impaired defoaming performance of the silicone oil compound, and a viscosity higher than the upper limit value will cause the viscosity of the silicone oil compound to increase such that an unfavorable workability will be resulted.

Preferable examples of the organopolysiloxane represented by the above general formula (3) include dimethylpolysiloxane, diethylpolysiloxane, methylphenylpolysiloxane, dimethylsiloxane-diphenylsiloxane copolymer, methyl (3,3,3-trifluoropropyl) polysiloxane and α,ω-dihydroxydimethyl polysiloxane.

((b) Fine Powdered Silica)

Any known fine powdered silica may be used. For example, there may be used a wet silica such as a precipitated silica; and a dry silica such as a silica xerogel and a fumed silica. The aforementioned silicas are all hydrophilic silicas. In the present invention, these hydrophilic silicas may be directly used as they are, or there may be used hydrophobic silicas obtained by surface treating such hydrophilic silicas with a compound having an organic silyl group(s). Such fine powdered silica may be used singularly, or two or more kinds of them may be used in combination.

A commercially available fine powdered silica may be used. Examples of such fine powdered silica include, by product names, AEROSIL™ (by NIPPON AEROSIL Co., Ltd.); Nipsil™ and NIPGEL™ (by TOSOH SILICA CORPORATION); and Sylysia™(by FUJI SILYSIA CHEMICAL Ltd.) The fine powdered silica exhibits a specific surface area of not smaller than 100 m²/g by BET method. Particularly, it is preferred that such fine powdered silica exhibit a specific surface area of not smaller than 150 m²/g, more preferably a specific surface area of 150 to 500 m²/g, by BET method.

It is preferred that such fine powdered silica be in an amount of 0.1 to 30 parts by mass, 0.1 to 20 parts by mass, 1 to 20 parts by mass, particularly 2 to 15 parts by mass with respect to 100 parts by mass of the organopolysiloxane (a). The defoaming performance will be impaired if the fine powdered silica is in an excessively small amount; whereas an excessively large amount of such fine powdered silica will cause the viscosity of the silicone oil compound to increase such that an unfavorable workability will be resulted.

<Preparation of Silicone Oil Compound>

A silicone oil compound may be prepared according to a known method. For example, such silicone oil compound may be obtained as follows. That is, the organopolysiloxane (a) and the fine powdered silica (b) may be mixed together, followed by performing a heating treatment at a temperature of a room temperature to 200° C., and later performing neutralization and/or removing low-boiling fractions if necessary. There may be further added to such silicone oil compound, for example, an inorganic ammonium salt, an organic silicon compound, a siloxane resin and an alkali catalyst that are disclosed in Japanese examined patent application publication No. Hei 4-42043, JP-A-Hei 5-261206 and JP-A-2005-324140, for the purpose of improving the defoaming agent's defoaming persistence, high-temperature properties, dilution stability, alkali resistance and the like.

<(C) Polyoxyalkylene-Modified Organopolysiloxane>

A polyoxyalkylene-modified organopolysiloxane serving as the defoaming agent composition of the present invention is used to emulsify and disperse in an aqueous system the Gemini-type alkyl-polyoxyalkylene-modified silicone (A), a later-described polyoxyalkylene polymer (D) and the silicone oil compound (B). A preferable example of such polyoxyalkylene-modified organopolysiloxane is the one represented by the following general formula (4).

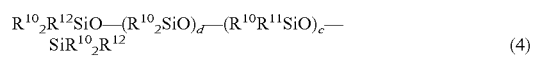

$$R^{10}{}_2 R^{12} SiO—(R^{10}{}_2 SiO)_d—(R^{10}R^{11}SiO)_e— SiR^{10}{}_2 R^{12} \quad (4)$$

In the above general formula (4), those represented by $R^{10}$ are substituted or unsubstituted monovalent hydrocarbon groups each having 1 to 18 carbon atoms and being either identical to or different from one another. Specific examples of such monovalent hydrocarbon group include an alkyl group such as a methyl group, an ethyl group, a propyl group, an isopropyl group, a butyl group, an isobutyl group, a pentyl group, a hexyl group, a heptyl group, an octyl group, a nonyl group, a decyl group, a dodecyl group, a tridecyl group, a tetradecyl group, a hexadecyl group and an octadecyl group; a cycloalkyl group such as a cyclohexyl group; an alkenyl group such as a vinyl group and an allyl group; an aryl group such as a phenyl group and a tolyl group; and an aralkyl group such as a styryl group and an α-methylstyryl group. Examples of such monovalent hydrocarbon group also include a chloromethyl group, a 3-chloropropyl group, a 3,3,3-trifluoropropyl group, a cyanoethyl group, a 3-aminopropyl group and a N-(β-aminoethyl)-γ-aminopropyl group that are obtained by substituting a part of or all the hydrogen atoms bonded to the carbon atoms in the aforementioned groups with, for example, a halogen atom, a cyano group and/or an amino group.

Further, is a polyoxyalkylene group represented by the following general formula (5).

$$-R^{13}-O-(CH_2CH_2O)_f-(CH_2CH(CH_3)O)_g-Q \quad (5)$$

In the above general formula (5), $R^{13}$ represents a divalent hydrocarbon group having 2 to 6 carbon atoms. Examples of such divalent hydrocarbon group include alkylene and alkenylene groups such as an ethylene group, a propylene group, a butylene group, a pentylene group and a hexylene group. Moreover, Q represents a hydrogen atom, an alkyl group having 1 to 6 carbon atoms, an acetyl group or an isocyan group. Examples of such alkyl group include a methyl group, an ethyl group, a propyl group, a butyl group and a pentyl group. f is a number satisfying f>0, and g is a number satisfying g≥0, provided that f and g are positive numbers satisfying 3≤f+g≤80, preferably 5≤f+g≤60; and f/g=2/8 to 10/0, preferably f/g=3/8 to 8/3.

Meanwhile, $R^{12}$ represents a group similar to $R^{10}$ or $R^{11}$, a hydroxyl group or an alkoxy group having 1 to 6 carbon atoms. Specific examples of $R^{12}$ include the groups listed above as the examples of $R^{10}$ and $R^{11}$, and examples of such alkoxy group include a methoxy group, an ethoxy group, a propoxy group and a butoxy group.

Here, in the general formula (4), d represents an integer of 5 to 200, preferably an integer of 20 to 150; e represents an integer of 1 to 30, preferably an integer of 1 to 20.

Such polyoxyalkylene-modified organopolysiloxane may be used singularly, or there may be used a mixture of two or more kinds of such polyoxyalkylene-modified organopolysiloxane. There can be used a polyoxyalkylene-modified organopolysiloxane(s) exhibiting a viscosity of 10 to 10,000 mm$^2$/s, preferably 50 to 8,000 mm$^2$/s, more preferably 500 to 5,000 mm$^2$/s, when measured by an Ostwald viscometer at 25° C.

Specific examples of such polyoxyalkylene-modified organopolysiloxane include, but are not limited to the following ones.

$(CH_3)_3SiO-[(CH_3)_2SiO]_{30}-[(CH_3)R'SiO]_5-Si(CH_3)_3$
$R':-C_3H_6O-(C_2H_4O)_{30}-(C_3H_6O)_{10}-C_4H_9$,
$(CH_3)_3SiO-[(CH_3)_2SiO]_{30}-[(CH_3)R'SiO]_3-Si(CH_3)_3$
$R':-C_3H_6O-(C_2H_4O)_{20}-(C_3H_6O)_{20}-C_4H_9$,
$(CH_3)_3SiO-[(CH_3)_2SiO]_{40}-[(CH_3)R'SiO]_4-Si(CH_3)_3$
$R':-C_3H_6O-(C_2H_4O)_{21}-(C_3H_6O)_7-COCH_3$,
$(CH_3)_3SiO-[(CH_3)_2SiO]_{50}-[(CH_3)R''SiO]_6-[(CH_3)R'''SiO]_1-Si(CH_3)_3$
$R'':-C_3H_6O-(C_2H_4O)_{32}-(C_3H_6O)_8-C_4H_9$,
$R''':-C^{12}H^{25}$,
$(CH_3)_3SiO-[(CH_3)_2SiO]_{135}-[(CH_3)R'SiO]_{15}-Si(CH_3)_3$

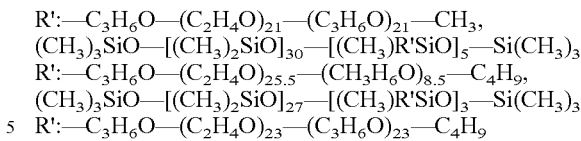

$R':-C_3H_6O-(C_2H_4O)_{21}-(C_3H_6O)_{21}-CH_3$,
$(CH_3)_3SiO-[(CH_3)_2SiO]_{30}-[(CH_3)R'SiO]_5-Si(CH_3)_3$
$R':-C_3H_6O-(C_2H_4O)_{25.5}-(CH_3H_6O)_{8.5}-C_4H_9$,
$(CH_3)_3SiO-[(CH_3)_2SiO]_{27}-[(CH_3)R'SiO]_3-Si(CH_3)_3$
$R':-C_3H_6O-(C_2H_4O)_{23}-(C_3H_6O)_{23}-C_4H_9$

As such polyoxyalkylene-modified organopolysiloxane, there may also be used a polyoxyalkylene-modified organopolysiloxane that is commercially available. Particularly, such polyoxyalkylene-modified organopolysiloxane can be easily obtained by a conventional and known method where, for example, a polyoxyalkylene compound having at its molecular chain terminal(s) an unsaturated group such as a vinyl group or a allyl group is added to an organopolysiloxane containing SiH groups under the presence of a platinum catalyst.

Here, other than an organopolysiloxane that has been modified by a single polyoxyalkylene compound, there may also be used a silicone oil containing within an identical molecule two or more kinds of polyoxyalkylene groups with, for example, different molar ratios of ethyleneoxy group/propyleneoxy group or different molecular weights of polyoxyalkylene groups; and two or more kinds of polyoxyalkylene-modified silicone oil with different structures.

The polyoxyalkylene-modified organopolysiloxane (C) is added in an amount of 1 to 95% by mass, preferably 1 to 60% by mass, more preferably 5 to 40% by mass, with respect to 100% by mass of the defoaming agent composition of the present invention. A water dispersibility will be impaired if such polyoxyalkylene-modified organopolysiloxane (C) is added in an amount of smaller than 1% by mass. Meanwhile, an inferior defoaming performance will be resulted if the polyoxyalkylene-modified organopolysiloxane (C) is added in an amount of greater than 95% by mass.

<(D) Polyoxyalkylene Polymer>

A polyoxyalkylene polymer (D) serves as a dispersion aid for improving the dispersibilities of the component (B) as well as the components (A) and (C). The component (D) can be added to the composition of the present invention as an optional ingredient. Such component (D) may be used singularly, or two or more kinds thereof may be used in combination. One example of such polyoxyalkylene polymer (D) is represented by the following general formula (6)

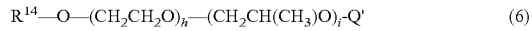

$$R^{14}-O-(CH_2CH_2O)_h-(CH_2CH(CH_3)O)_i-Q' \quad (6)$$

When the above $R^{14}$ is a monovalent organic group, examples of such group include an alkyl group such as a methyl group, an ethyl group, a propyl group and a butyl group; an alkenyl group such as a vinyl group and an allyl group; and an acyl group such as an acetyl group and a stearoyl group.

Further, in the above general formula (6), Q' represents a hydrogen atom, an alkyl group having 1 to 6 carbon atoms, an acetyl group or an isocyan group. Examples of such alkyl group include a methyl group, an ethyl group, a propyl group, a butyl group and a pentyl group. h is a number satisfying h>0, i is a number satisfying i≥0, provided that h and i are positive numbers satisfying 3≤h+i≤80, preferably 5≤h+i≤60; and h/i=2/8 to 10/0, preferably h/i=3/8 to 8/3.

A weight-average molecular weight of the component (D) measured by GPC is preferably 500 to 10,000, more preferably 1,000 to 5,000, in terms of polystyrene. When such weight-average molecular weight is within these ranges, the defoaming agent composition obtained may easily exhibit a favorable product stability; and a favorable workability due to the fact that a high viscosity is unlikely to be achieved under such condition.

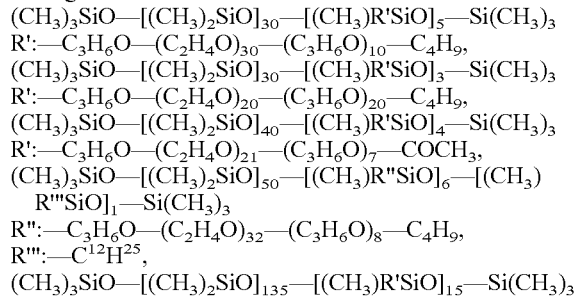

Specific examples of such polyoxyalkylene polymer as the component (D) include, but are not limited to the following ones.

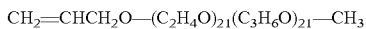

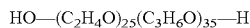

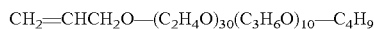

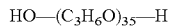

As for the defoaming agent composition of the present invention, the component (D) is added in an amount of 0 to 80% by mass, preferably 0 to 50% by mass, with respect to the whole defoaming agent composition. The product stability of the defoaming agent composition obtained may easily deteriorate if the component (D) is added in an amount of greater than 80% by mass. Here, if adding such component (D), it may be simply added in an effective amount capable of improving the dispersibility of the component (B). Particularly, it is preferred that the component (D) be added in an amount of not smaller than 5% by mass.

<Other Components>

Components other than those described above may also be added to the defoaming agent composition of the present invention if necessary, without impairing the purposes of the present invention. For example, a small amount of a preservative/sterilizer may be added to the defoaming agent composition for preservation purposes. Specific examples of such preservative/sterilizer include sodium hypochlorite, a sorbic acid, potassium sorbate, a salicylic acid, sodium salicylate, a benzoic acid, sodium benzoate, parabens and an isothiazoline compound. These components may be preferably added in an amount of 0 to 0.5% by mass with respect to the whole defoaming agent composition.

<Method for Using Composition>

The present invention also provides a method for defoaming a liquid, which includes a step of adding to a liquid the defoaming agent composition of the present invention containing the components (A) to (D) of the given amounts. Examples of such liquid include a liquid comprised of a single ingredient, a solution, an emulsion and a suspension. Further, although such liquid may be either an aqueous liquid or an oily liquid, an aqueous liquid is preferred. Examples of such aqueous liquid include a pesticide, a scouring agent and an aqueous cutting oil. In the defoaming method of the present invention, the defoaming agent composition of the present invention is normally added in an amount of 0.01 to 5 parts by mass, preferably 0.05 to 1 parts by mass with respect to 100 parts by mass of the above-mentioned liquid.

WORKING EXAMPLE

The present invention is described in detail hereunder with reference to working examples. However, the present invention is not limited to the following working examples. Further, the viscosities mentioned in the working examples are values measured by a Cannon-Fenske viscometer (SO) (type name: No. 500 by SIBATA SCIENTIFIC TECHNOLOGY LTD.) at 25° C.

Working Example 1

(I) Production of Ricinoleic Acid-polyoxyethylene Condensate

Figure 2:
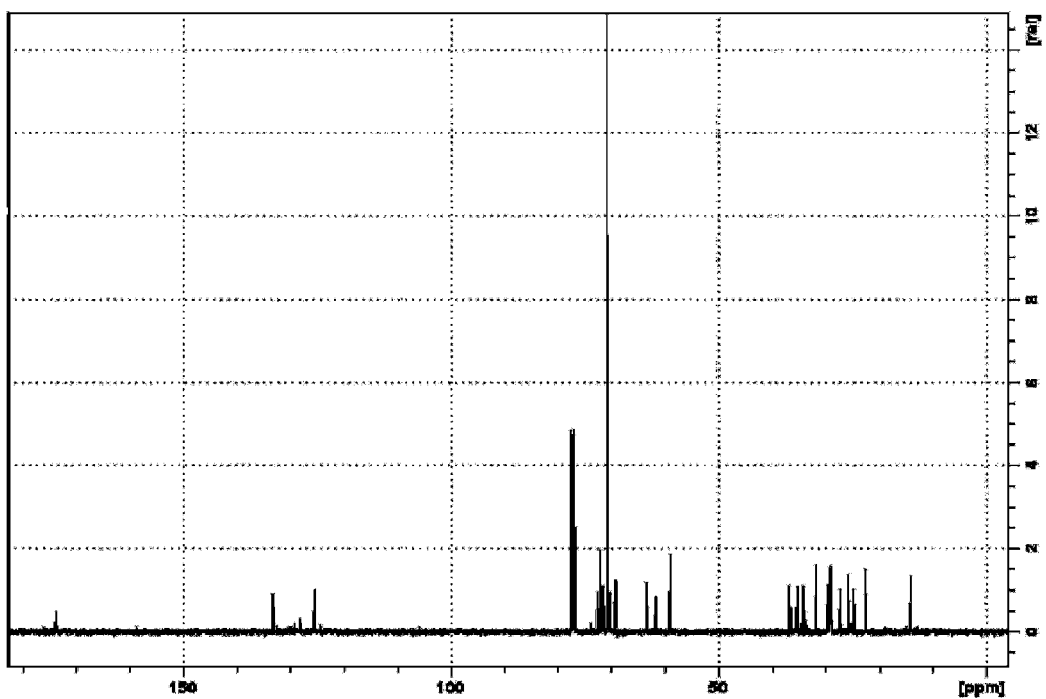
FIG. 2 is a $^{13}$C-NMR spectrum of the ricinoleic acid-polyoxyethylene condensate obtained in (1) of the working example 1.

In a flask equipped with a thermometer, a cooling tube, a dean-stark apparatus and a stirrer, a castor oil fatty acid CO-FA S (by ITOH OIL CHEMICALS CO., LTD., ricinoleic acid 90%) of 218 g and UNIOX M 1000 (by NOF CORPORATION, polyoxyethylene glycol monomethyl ether, weight-average molecular weight 1,000) of 877 g were solved into toluene of 1,096 g. A paratoluenesulfonate monohydrate of 1.4 g was further added thereto as a catalyst, followed by performing heating until a temperature of 120° C. had been reached, and then performing refluxing for 7 hours to distill away water generated as a by-product. Heating was then stopped to allow cooling to take place until a room temperature (25° C.) had been reached. Next, sodium hydrogen carbonate of 7.3 g and sodium sulfate of 14.7 g were added to perform stirring for 2 hours under room temperature, thus completing neutralization and dehydration. Heating was again performed until a temperature of 120° C. had been reached, and the solvent was distilled away under a reduced pressure of not higher than 10 mmHg. Further, a filtration plate (NA-10 by Advantec) was used to perform pressure filtration, thus obtaining 1,018 g (yield 93%) of a ricinoleic acid-polyoxyethylene condensate as a reaction product having an average structure represented by the following formula (7). Here, a $^1$H-NMR chart is shown in FIG. 1; and a $^{13}$C-NMR chart is shown in FIG. 2.

[Chemical formula 11]

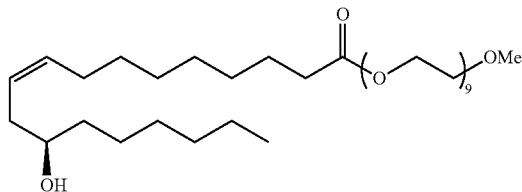

(7)

(II) Production of Gemini-Type Alkyl-Polyoxyethylene-Modified Silicone

The ricinoleic acid-polyoxyethylene condensate of 310 g obtained in (I) and toluene of 498 g were loaded into a flask equipped with a thermometer, a cooling tube and a stirrer, followed by heating the same to a temperature of 130° C., and then adding thereto a platinum catalyst of 1 g (by Shin-Etsu Chemical Co., Ltd., PL-50T, toluene solution of vinylsiloxane complex of chloroplatinic acid (platinum metal concentration of 0.5% by mass)). Further, 187 g of an organopolysiloxane having an average structure represented by the following formula (8) and having at both terminals a hydrosilyl group was then gradually delivered thereinto by drops for 15 min.

[Chemical formula 12]

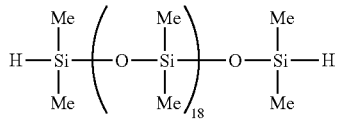

(8)

Figure 3:
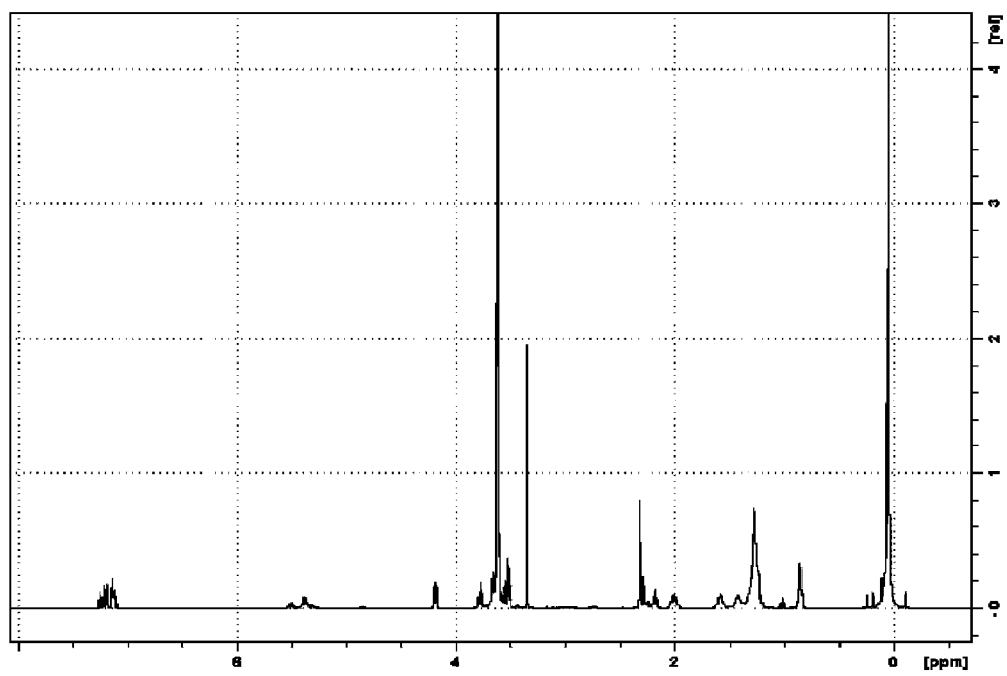
FIG. 3 is a $^1$H-NMR spectrum of a Gemini-type alkyl-polyoxyethylene-modified silicone obtained in (2) of the working example 1.
Figure 4:
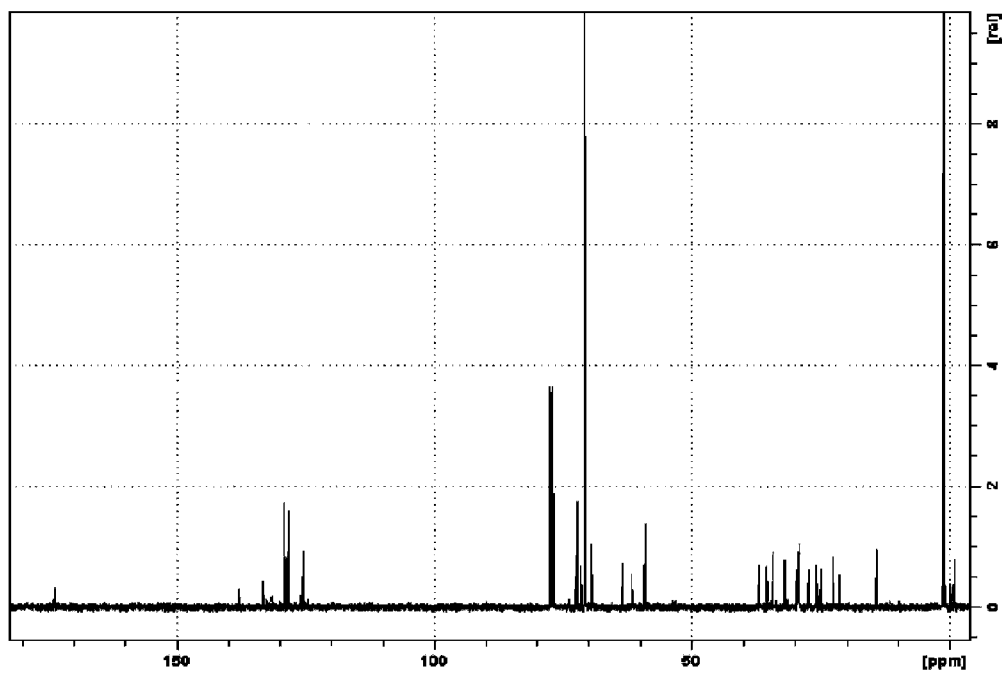
FIG. 4 is a $^{13}$C-NMR spectrum of the Gemini-type alkyl-polyoxyethylene-modified silicone obtained in (2) of the working example 1.

After the dripping had been completed, maturing was performed for 6 hours while maintaining the inner temperature of 130° C. There, a reduced pressure of not higher than 10 mmHg was employed to distill away the solvent as the reaction appearance had turned clear, followed by allowing cooling to take place until the room temperature (25° C.) had been reached, and then using the filtration plate (NA-10 by Advantec) to perform pressure filtration to obtain 453 g (yield 91%) of a Gemini-type alkyl-polyoxyethylene-modified silicone as a reaction product having an average structure represented by the following formula (9). Here, a $^1$H-NMR chart is shown in FIG. 3; and a $^{13}$C-NMR chart is shown in FIG. 4.

[Chemical formula 13]

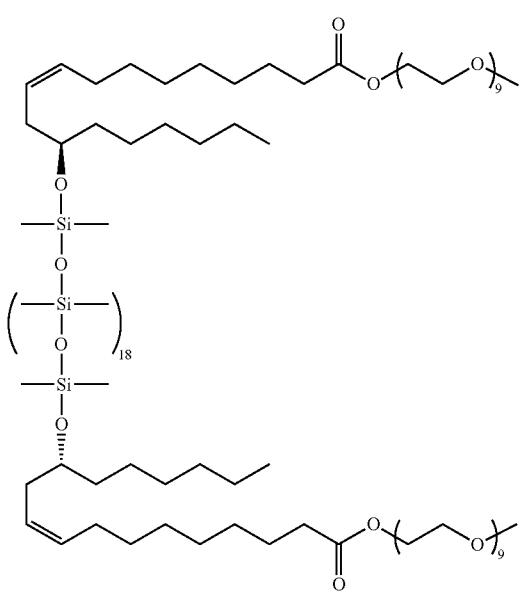

(9)

Working Example 2

(III) Production of Ricinoleic Acid-Polyoxyalkylene Condensate

Figure 5:
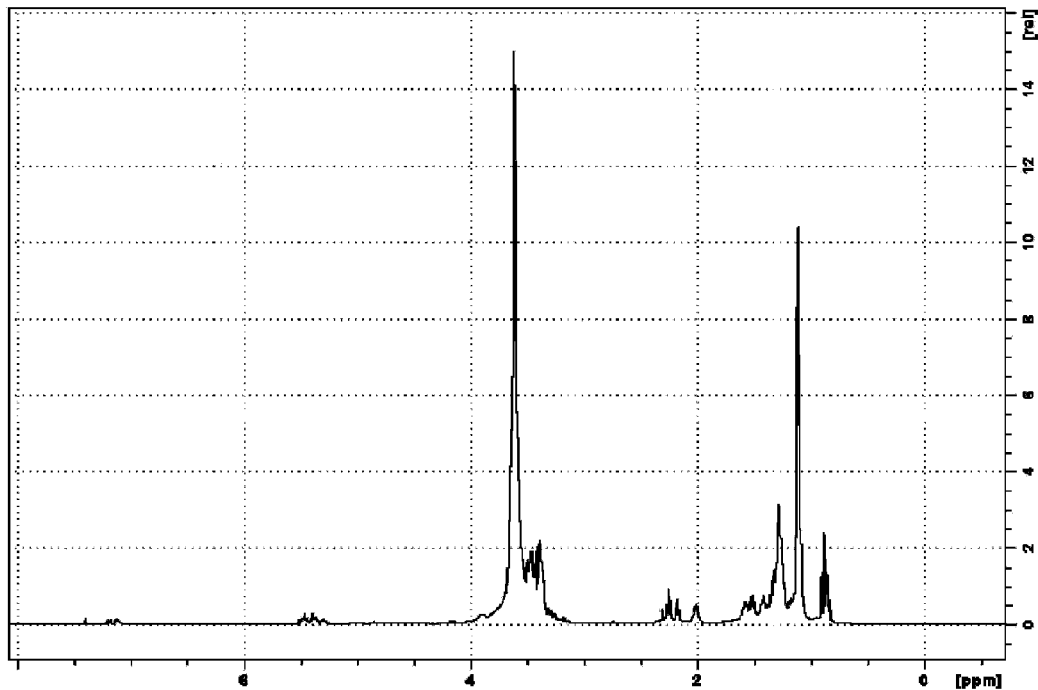
FIG. 5 is a $^1$H-NMR spectrum of a ricinoleic acid-polyoxyalkylene condensate obtained in (3) of a working example 2.
Figure 6:
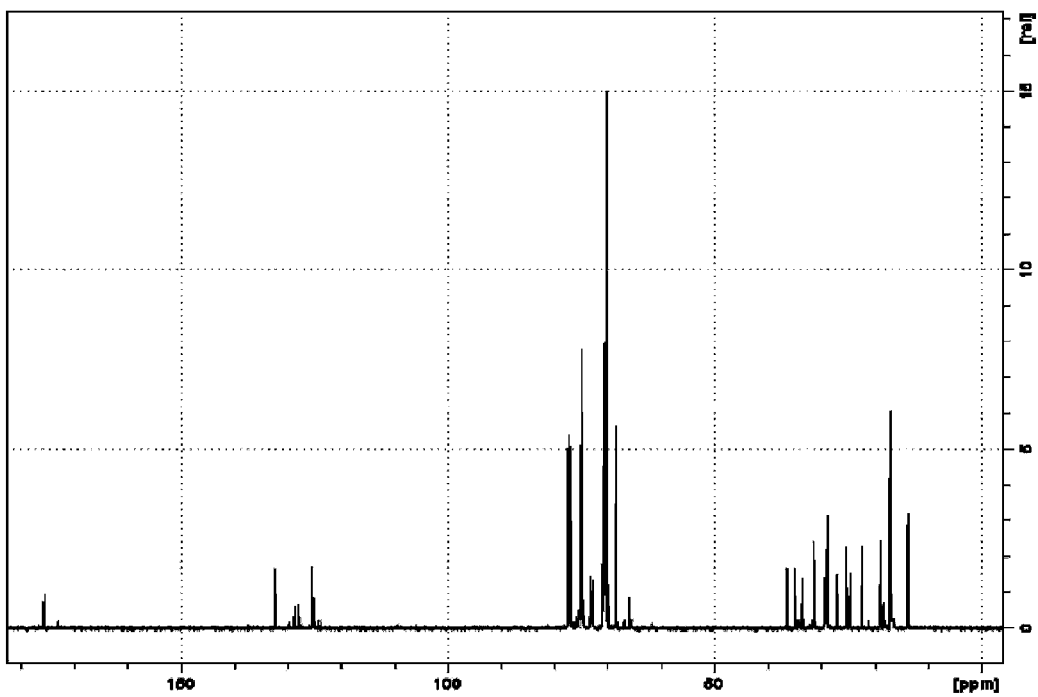
FIG. 6 is a $^{13}$C-NMR spectrum of the ricinoleic acid-polyoxyalkylene condensate obtained in (3) of the working example 2.

In a flask equipped with a thermometer, a cooling tube, a dean-stark apparatus and a stirrer, a castor oil fatty acid CO-FA S (by ITOH OIL CHEMICALS CO., LTD., ricinoleic acid 90%) of 280 g and UNILUBE 50 MB-11 (by NOF CORPORATION, polyoxyethylene (9) polyoxypropylene (11) monobutylether) of 1,184 g were solved into toluene of 1,465 g. A paratoluenesulfonate monohydrate of 1.78 g was further added thereto as a catalyst, followed by performing heating until a temperature of 120° C. had been reached, and then performing refluxing for 7 hours to distill away water generated as a by-product. Heating was then stopped to allow cooling to take place until a room temperature (25° C.) had been reached. Next, sodium hydrogen carbonate of 9.4 g and sodium sulfate of 18.8 g were added to perform stirring for 2 hours under room temperature, thus completing neutralization and dehydration. Heating was again performed until a temperature of 120° C. had been reached, and the solvent was distilled away under a reduced pressure of not higher than 10 mmHg. Further, a filtration plate (NA-10 by Advantec) was used to perform pressure filtration, thus obtaining 1,391 g (yield 95%) of a ricinoleic acid-polyoxyalkylene condensate as a reaction product having an average structure represented by the following formula (10). Here, a $^1$H-NMR chart is shown in FIG. 5; and a $^{13}$C-NMR chart is shown in FIG. 6.

[Chemical formula 14]

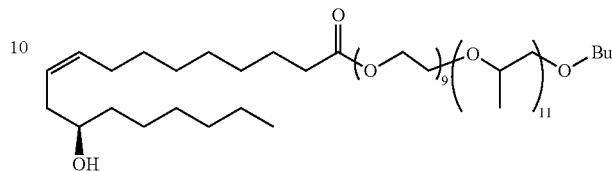

(10)

Figure 7:
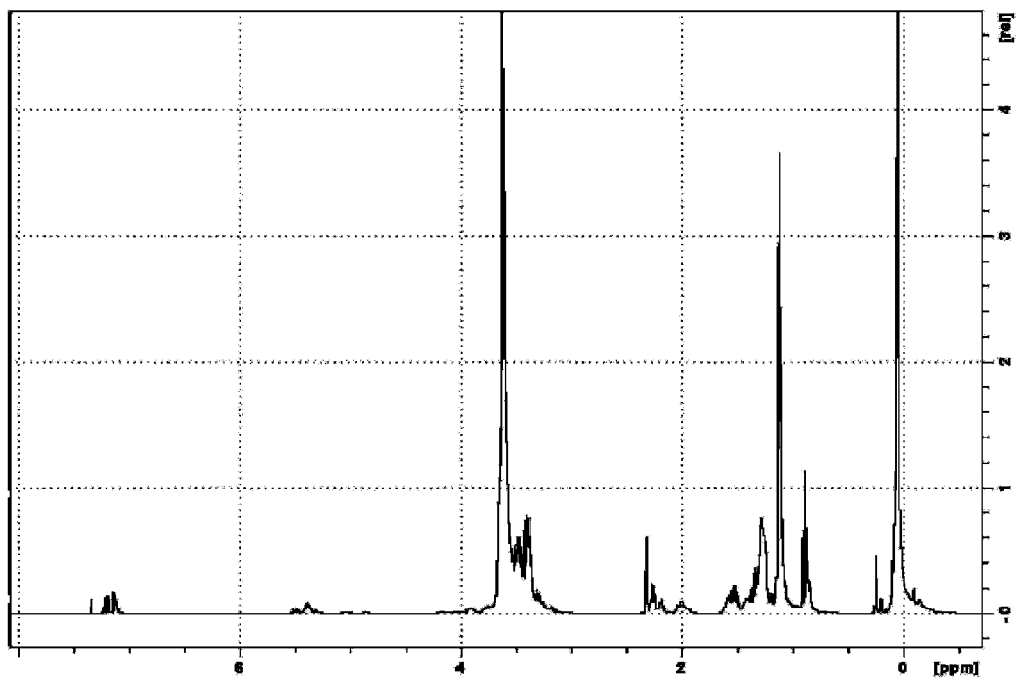
FIG. 7 is a $^1$H-NMR spectrum of a Gemini-type alkyl-polyoxyalkylene-modified silicone obtained in (4) of the working example 2.
Figure 8:
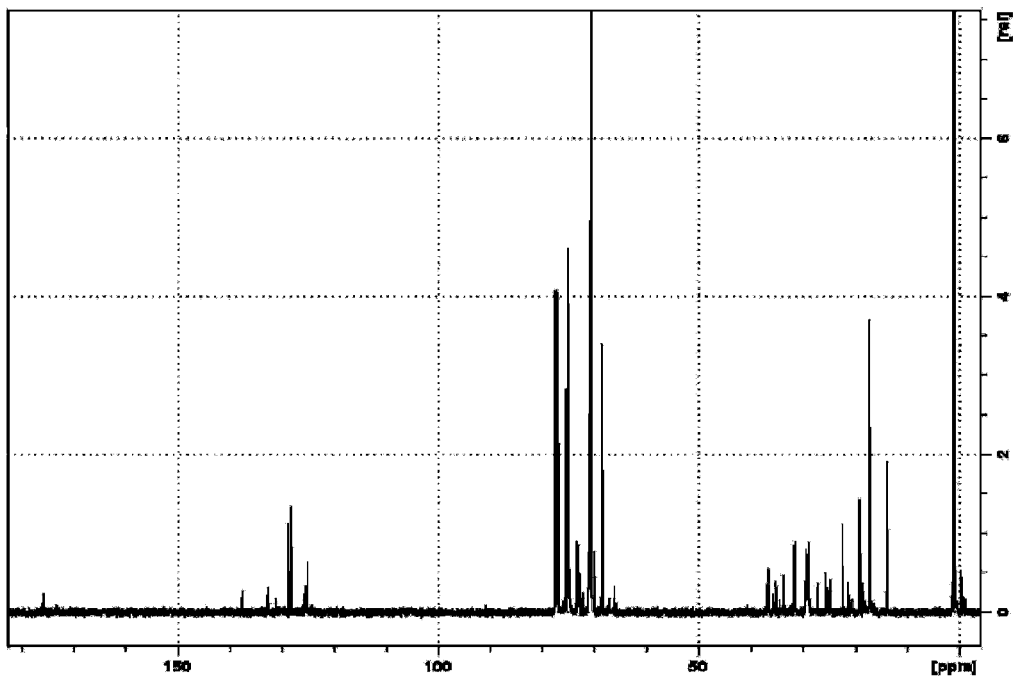
FIG. 8 is a $^{13}$C-NMR spectrum of the Gemini-type alkyl-polyoxyalkylene-modified silicone obtained in (4) of the working example 2.

(IV) Production of Gemini-type Alkyl-polyoxyalkylene-modified Silicone by Dehydrogenation-addition Reaction with Both-terminated Organohydrogenpolysiloxane The ricinoleic acid-polyoxyalkylene condensate of 320 g obtained in (III) and toluene of 500 g were loaded into a flask equipped with a thermometer, a cooling tube and a stirrer, followed by heating the same to a temperature of 130° C., and then adding thereto a platinum catalyst of 1 g (by Shin-Etsu Chemical Co., Ltd., PL-50T, toluene solution of vinylsiloxane complex of chloroplatinic acid (platinum metal concentration of 0.5% by mass)). Further, 178 g of a both-terminated organohydrogenpolysiloxane having an average structure represented by the above formula (8) was then gradually delivered thereinto by drops for 15 min. After the dripping had been completed, maturing was performed for 6 hours while maintaining the inner temperature of 130° C. There, a reduced pressure of not higher than 10 mmHg was employed to distill away the solvent as the reaction appearance had turned clear, followed by allowing cooling to take place until the room temperature (25° C.) had been reached, and then using the filtration plate (NA-10 by Advantec) to perform pressure filtration to obtain 463 g (yield 93%) of a Gemini-type alkyl-polyoxyalkylene-modified silicone as a reaction product having an average structure represented by the following formula (11). Here, a $^1$H-NMR chart is shown in FIG. 7; and a $^{13}$C-NMR chart is shown in FIG. 8.

[Chemical formula 15]

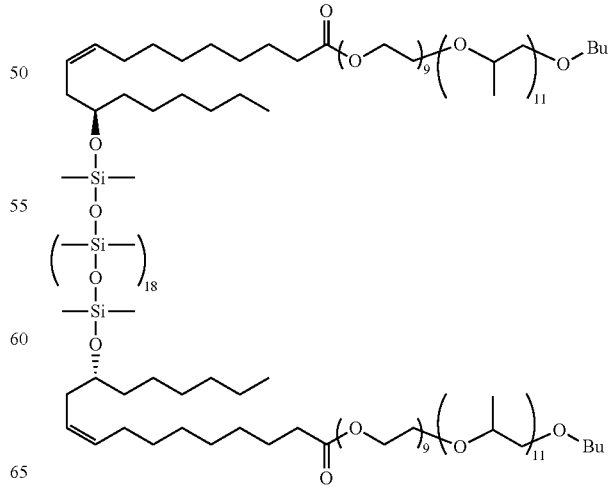

(11)

(V) Production of Gemini-type Alkyl-polyoxyethylene-modified Silicone by Dealcoholization Reaction with Both-terminated Ethoxy-modified Organopolysiloxane The ricinoleic acid-polyoxyalkylene condensate of 400 g obtained in (III) and toluene of 498 g were loaded into a flask equipped with a thermometer, a cooling tube, a dean-stark apparatus and a stirrer, followed by heating the same to a temperature of 130° C., and then adding thereto 1 g of a trifluoroacetic acid; 0.1 g of potassium acetate; and a total amount of 98 g of a both-terminated ethoxy-modified organopolysiloxane having an average structure represented by the following formula (12), which was delivered at once.

[Chemical formula 16]

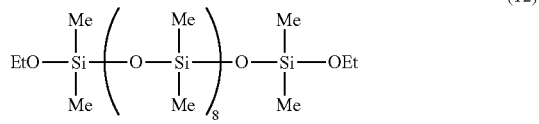

(12)

Figure 9:
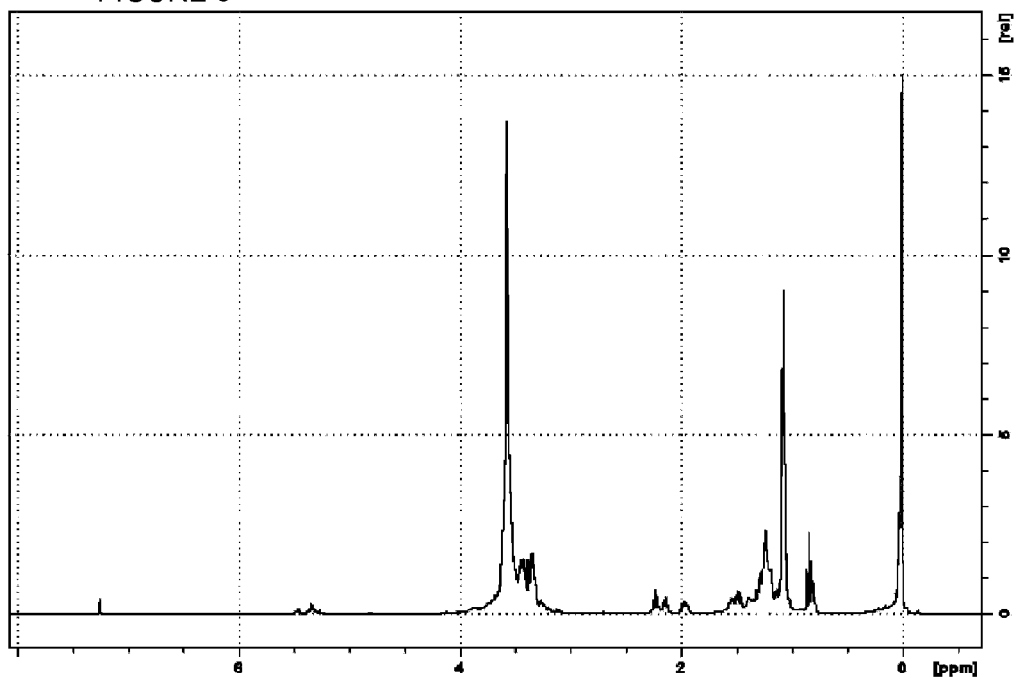
FIG. 9 is a $^1$H-NMR spectrum of a Gemini-type alkyl-polyoxyalkylene-modified silicone obtained in (5) of the working example 2.
Figure 10:
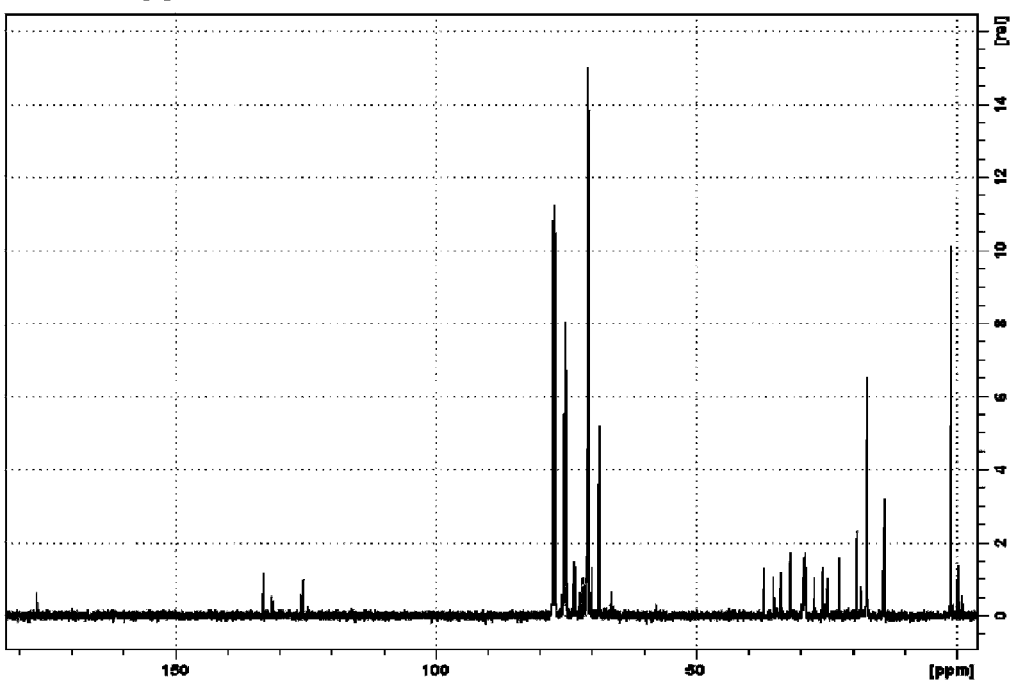
FIG. 10 is a $^{13}$C-NMR spectrum of the Gemini-type alkyl-polyoxyalkylene-modified silicone obtained in (5) of the working example 2.

After performing maturing for 2 hours while maintaining the inner temperature of 130° C., the solvent was distilled away by an amount of 150 g, and toluene of 150 g was added instead to again perform maturing for another 2 hours. Such solvent replacement operation was repeated twice, followed by allowing cooling to take place until a temperature of 40° C. had been reached. Sodium hydrogen carbonate of 5 g and sodium sulfate of 7.5 g were then added to perform stirring for 2 hours, thus completing neutralization and dehydration. Heating was again performed until a temperature of 120° C. had been reached, and the solvent was then distilled away under a reduced pressure of not higher than 10 mmHg. By using the filtration plate (NA-10 by Advantec) to perform pressure filtration, there was then obtained 468 g (yield 94%) of a Gemini-type alkyl-polyoxyalkylene-modified silicone as a reaction product having an average structure represented by the following formula (13). Here, a $^1$H-NMR chart is shown in FIG. 9; and a $^{13}$C-NMR chart is shown in FIG. 10.

[Chemical formula 17]

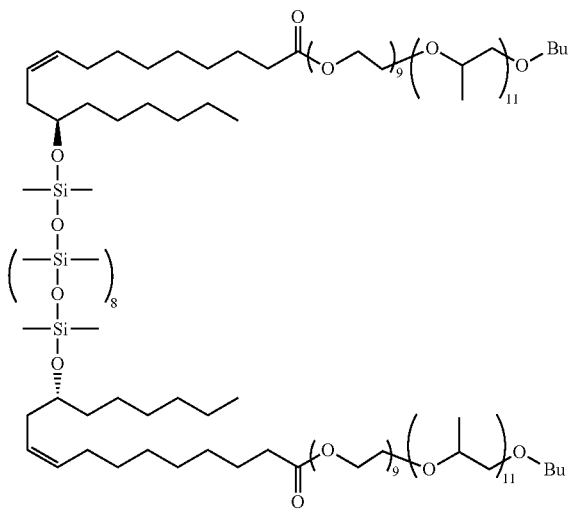

(13)

Working Example 3

(VI) Production of Ricinoleic Acid-polyoxyalkylene Condensate

A hydroxy fatty acid ester CO-FA methylester (by ITOH OIL CHEMICALS CO., LTD., methyl ricinoleate) of 344 g and UNILUBE 50 MB-11 (by NOF CORPORATION, polyoxyethylene (9) polyoxypropylene (11) monobutylether) of 1,000 g were loaded into a flask equipped with a thermometer, a cooling tube, a dean-stark apparatus and a stirrer, followed by adding thereto 1.4 g of tetraisopropyl titanium as a catalyst. After achieving a reduced pressure of not higher than 20 mmHg by a vacuum pump, heating was performed until a temperature of 120° C. had been reached, the temperature being maintained for 6 hours thereafter. Heating was then stopped to allow cooling to take place until a room temperature (25° C.) had been reached. After reaching room temperature, the pressure was restored to a normal pressure, followed by using the filtration plate (NA-10 by Advantec) to perform pressure filtration to obtain 1,236 g (yield 92%) of a ricinoleic acid-polyoxyalkylene condensate as a reaction product having an average structure represented by the above formula (10).

(VII) Production of Gemini-type Alkyl-polyoxyalkylene-modified Silicone by Dehydrogenation-addition Reaction with Both-terminated Organohydrogenpolysiloxane The ricinoleic acid.polyoxyalkylene condensate of 320 g obtained in (VI) and toluene of 500 g were loaded into a flask equipped with a thermometer, a cooling tube and a stirrer, followed by heating the same to a temperature of 130° C., and then adding thereto a platinum catalyst of 1 g (by Shin-Etsu Chemical Co., Ltd., PL-50T, toluene solution of vinylsiloxane complex of chloroplatinic acid (platinum metal concentration of 0.5% by mass)). Further, 178 g of a both-terminated organohydrogenpolysiloxane having an average structure represented by the above formula (8) was then gradually delivered thereinto by drops for 15 min. After the dripping had been completed, maturing was performed for 6 hours while maintaining the inner temperature of 130° C. There, a reduced pressure of not higher than 10 mmHg was employed to distill away the solvent as the reaction appearance had turned clear, followed by allowing cooling to take place until the room temperature (25° C.) had been reached, and then using the filtration plate (NA-10 by Advantec) to perform pressure filtration to obtain 473 g (yield 95%) of a Gemini-type alkyl-polyoxyalkylene-modified silicone as a reaction product having an average structure represented by the above formula (11).

Working Example 4

(VIII) Production of 12-hydroxystearic Acid-polyoxyalkylene condensate

Figure 11:
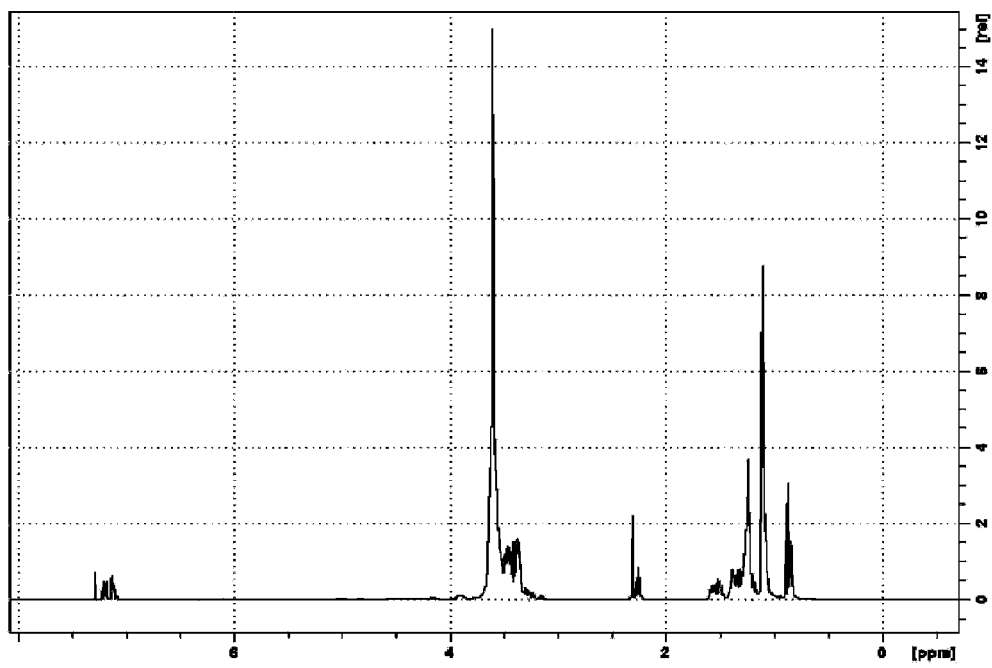
FIG. 11 is a $^1$H-NMR spectrum of a 12-hydroxystearic acid-polyoxyalkylene condensate obtained in (8) of a working example 4.

In a flask equipped with a thermometer, a cooling tube, a dean-stark apparatus and a stirrer, a 12-hydroxystearic acid (by ITOH OIL CHEMICALS CO., LTD.) of 150 g and UNILUBE 50 MB-11 (by NOF CORPORATION, polyoxyethylene (9) polyoxypropylene (11) monobutylether) of 630 g were solved into toluene of 780 g. A paratoluenesulfonate monohydrate of 0.95 g was further added thereto as a catalyst, followed by performing heating until a temperature of 120° C. had been reached, and then performing refluxing for 7 hours to distill away water generated as a by-product. Heating was then stopped to allow cooling to take place until a room temperature (25° C.) had been reached. Next, sodium hydrogen carbonate of 5 g and sodium sulfate of 10 g were added to perform stirring for 2 hours under room temperature, thus completing neutralization and dehydration. Heating was again performed until a temperature of 120° C. had been reached, and the solvent was distilled away under a reduced pressure of not higher than 10 mmHg. Further, a filtration plate (NA-10 by Advantec) was used to perform pressure filtration, thus obtaining 702 g (yield 90%) of a 12-hydroxystearic acid-polyoxyalkylene condensate as a reaction product having an average structure represented by the following formula (14). Here, a $^1$H-NMR chart is shown in FIG. 11.

[Chemical formula 18]

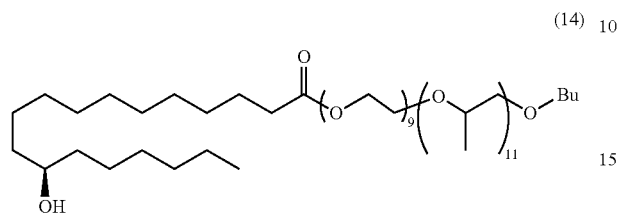

(14)

(IX) Production of Gemini-type Alkyl-polyoxyallcylene-modified Silicone

Figure 12:
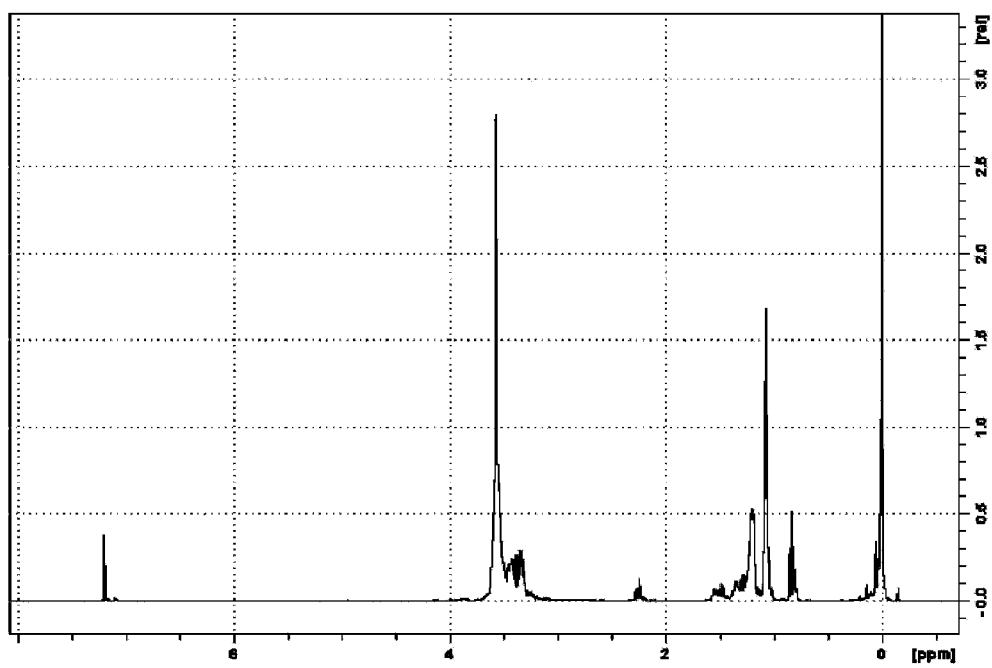
FIG. 12 is a $^1$H-NMR spectrum of a Gemini-type alkyl-polyoxyalkylene-modified silicone obtained in (9) of the working example 4.

The 12-hydroxystearic acid-polyoxyalkylene condensate of 200 g obtained in (VIII) and toluene of 320 g were loaded into a flask equipped with a thermometer, a cooling tube and a stirrer, followed by heating the same to a temperature of 130° C., and then adding thereto a platinum catalyst of 3.2 g (by Shin-Etsu Chemical Co., Ltd., PL-50T, toluene solution of vinylsiloxane complex of chloroplatinic acid (platinum metal concentration of 0.5% by mass)). Further, 117 g of a both-terminated organohydrogenpolysiloxane having an average structure represented by the above formula (8) was then gradually delivered thereinto by drops for 10 min. After the dripping had been completed, maturing was performed for 6 hours while maintaining the inner temperature of 130° C. There, a reduced pressure of not higher than 10 mmHg was employed to distill away the solvent as the reaction appearance had turned clear, followed by allowing cooling to take place until the room temperature (25° C.) had been reached, and then using the filtration plate (NA-10 by Advantec) to perform pressure filtration to obtain 285 g (yield 90%) of a Gemini-type alkyl-polyoxyalkylene-modified silicone as a reaction product having an average structure represented by the following formula (15). Here, a $^1$H-NMR chart is shown in FIG. 12.

[Chemical formula 19]

(15)

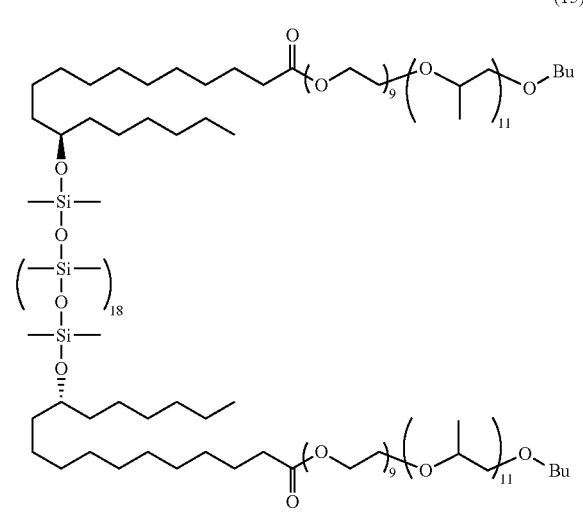

Working Example 5

(X) Production of Undecylenic Acid.Polyoxyethylene Condensate

In a flask equipped with a thermometer, a cooling tube, a dean-stark apparatus and a stirrer, an undecylenic acid (by ITOH OIL CHEMICALS CO., LTD.) of 133 g and UNIOX M 1000 (by NOF CORPORATION, polyoxyethylene glycol monomethyl ether, weight-average molecular weight 1,000) of 867 g were solved into toluene of 1,000 g. A paratoluenesulfonate monohydrate of 1.4 g was further added thereto as a catalyst, followed by performing heating until a temperature of 120° C. had been reached, and then performing refluxing for 7 hours to distill away water generated as a by-product. Heating was then stopped to allow cooling to take place until a room temperature (25° C.) had been reached. Next, sodium hydrogen carbonate of 7.3 g and sodium sulfate of 14.7 g were added to perform stirring for 2 hours under room temperature, thus completing neutralization and dehydration. Heating was again performed until a temperature of 120° C. had been reached, and the solvent was distilled away under a reduced pressure of not higher than 10 mmHg. Further, a filtration plate (NA-10 by Advantec) was used to perform pressure filtration, thus obtaining 910 g (yield 91%) of an undecylenic acid-polyoxyethylene condensate as a reaction product having an average structure represented by the following formula (16).

[Chemical formula 20]

(16)

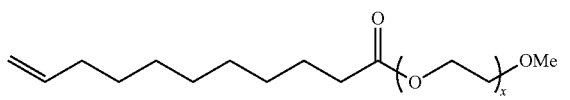

(XI) Production of Gemini-type Alkyl-polyoxyethylene-modified Silicone

The undecylenic acid-polyoxyethylene condensate of 318 g obtained in (X) and toluene of 500 g were loaded into a flask equipped with a thermometer, a cooling tube and a stirrer, followed by heating the same to a temperature of 130° C., and then adding thereto a platinum catalyst of 1 g (by Shin-Etsu Chemical Co., Ltd., PL-50T, toluene solution of vinylsiloxane complex of chloroplatinic acid (platinum metal concentration of 0.5% by mass)). Further, 182 g of an organopolysiloxane having an average structure represented by the above formula (8) and having at both terminals a hydrosilyl group was then gradually delivered thereinto by drops for 15 min. After the dripping had been completed, maturing was performed for 6 hours while maintaining the inner temperature of 130° C. There, a reduced pressure of not higher than 10 mmHg was employed to distill away the solvent as the reaction appearance had turned clear, followed by allowing cooling to take place until the room temperature (25° C.) had been reached, and then using the filtration plate (NA-10 by Advantec) to perform pressure filtration to obtain 461 g (yield 92%) of a Gemini-type alkyl-polyoxyethylene-modified silicone as a reaction product having an average structure represented by the following formula (17).

[Chemical formula 21]

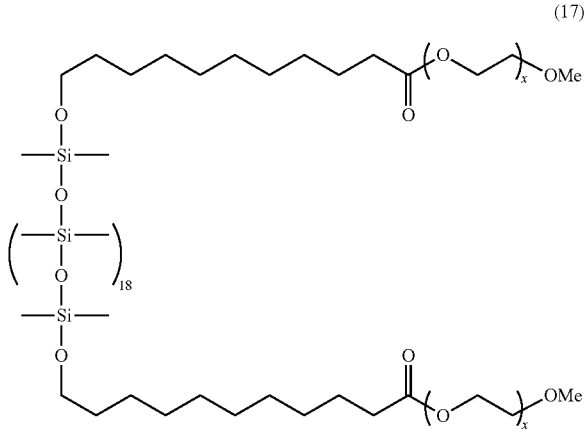

(17)

Working Example 6

(XII) Production of Undecylenic Acid-Polyoxyalkylene Condensate

An undecylenic acid (by ITOH OIL CHEMICALS CO., LTD.) of 133 g and UNILUBE 50 MB-11 (by NOF CORPORATION, polyoxyethylene (9) polyoxypropylene (11) monobutylether) of 867 g were loaded into a flask equipped with a thermometer, a cooling tube, a dean-stark apparatus and a stirrer, followed by adding thereto 1.1 g of tetraisopropyl titanium as a catalyst. After achieving a reduced pressure of not higher than 20 mmHg by a vacuum pump, heating was performed until a temperature of 120° C. had been reached, the temperature being maintained for 6 hours thereafter. Heating was then stopped to allow cooling to take place until a room temperature (25° C.) had been reached. After reaching such room temperature, the pressure was restored to a normal pressure, followed by using the filtration plate (NA-10 by Advantec) to perform pressure filtration to obtain 903 g (yield 90%) of an undecylenic acid-polyoxyalkylene condensate as a reaction product having an average structure represented by the following formula (18).

[Chemical formula 22]

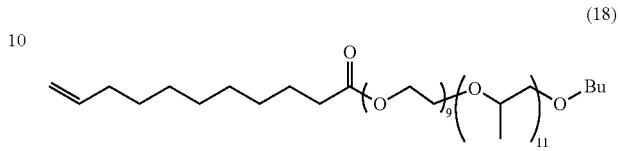

(18)

(XIII) Production of Gemini-type Alkyl-polyoxyalkylene-modified Silicone by Dehydrogenation-addition Reaction with Both-terminated Organohydrogenpolysiloxane The undecylenic acid-polyoxyalkylene condensate of 318 g obtained in (XII) and toluene of 500 g were loaded into a flask equipped with a thermometer, a cooling tube and a stirrer, followed by heating the same to a temperature of 130° C., and then adding thereto a platinum catalyst of 1 g (by Shin-Etsu Chemical Co., Ltd., PL-50T, toluene solution of vinylsiloxane complex of chloroplatinic acid (platinum metal concentration of 0.5% by mass)). Further, 182 g of a both-terminated organohydrogenpolysiloxane having an average structure represented by the above formula (8) was then gradually delivered thereinto by drops for 15 min. After the dripping had been completed, maturing was performed for 6 hours while maintaining the inner temperature of 130° C. There, a reduced pressure of not higher than 10 mmHg was employed to distill away the solvent as the reaction appearance had turned clear, followed by allowing cooling to take place until the room temperature (25° C.) had been reached, and then using the filtration plate (NA-10 by Advantec) to perform pressure filtration to obtain 458 g (yield 92%) of a Gemini-type alkyl-polyoxyalkylene-modified silicone as a reaction product having an average structure represented by the following formula (19).

[Chemical formula 23]

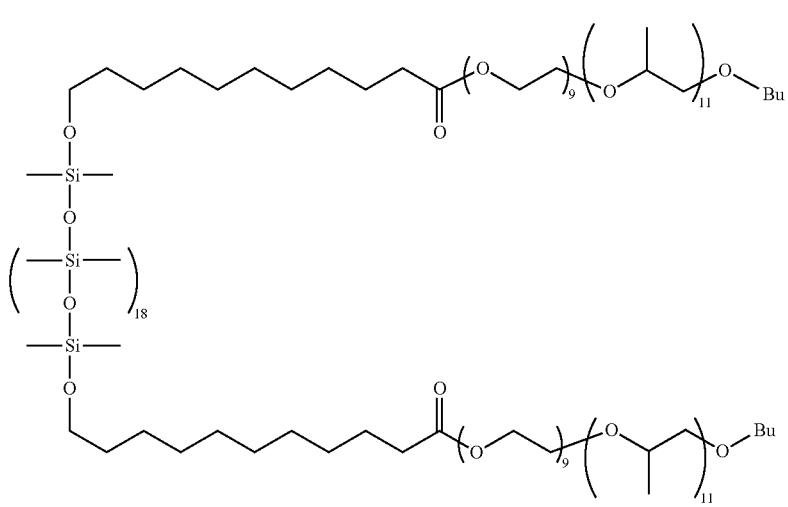

(19)

Working Example 7

(XIV) Production of Gemini-type Alkyl-polyoxyalkylene-modified Silicone

In a flask equipped with a thermometer, a cooling tube, a dean-stark apparatus and a stirrer, a castor oil fatty acid CO-FA S (by ITOH OIL CHEMICALS CO., LTD., ricinoleic acid 90%) of 175 g and UNILUBE 50 MB-26 (by NOF CORPORATION, polyoxyethylene (17) polyoxypropylene (17) monobutylether) of 1,274 g were solved into toluene of 1,451 g. A paratoluenesulfonate monohydrate of 1.78 g was further added thereto as a catalyst, followed by performing heating until a temperature of 120° C. had been reached, and then performing refluxing for 7 hours to distill away water generated as a by-product. Heating was then stopped to allow cooling to take place until a room temperature (25° C.) had been reached. Next, sodium hydrogen carbonate of 9.4 g and sodium sulfate of 18.8 g were added to perform stirring for 2 hours under room temperature, thus completing neutralization and dehydration. Heating was again performed until a temperature of 120° C. had been reached, and the solvent was distilled away under a reduced pressure of not higher than 10 mmHg. Further, a filtration plate (NA-10 by Advantec) was used to perform pressure filtration, thus obtaining 1,391 g (yield 95%) of a ricinoleic acid-polyoxyalkylene condensate as a reaction product having an average structure represented by the following formula (20).

[Chemical formula 24]

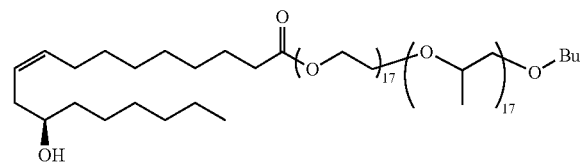

(20)

Next, such ricinoleic acid-polyoxyalkylene condensate of 115 g and toluene of 161 g were loaded into a flask equipped with a thermometer, a cooling tube and a stirrer, followed by heating the same to a temperature of 130° C., and then adding thereto diethylhydroxylamine of 1.6 g (by Aldrich). Further, 44.72 g of a both-terminated organohydrogenpolysiloxane having an average structure represented by the above formula (8) was then gradually delivered thereinto by drops for 5 min. After the dripping had been completed, maturing was performed for 6 hours while maintaining the inner temperature of 130° C. There, a reduced pressure of not higher than 10 mmHg was employed to distill away the solvent as the reaction appearance had turned clear, followed by allowing cooling to take place until the room temperature (25° C.) had been reached, and then using the filtration plate (NA-10 by Advantec) to perform pressure filtration to obtain 463 g (yield 93%) of a Gemini-type alkyl-polyoxyalkylene-modified silicone as a reaction product having an average structure represented by the following formula (21).

[Chemical formula 25]

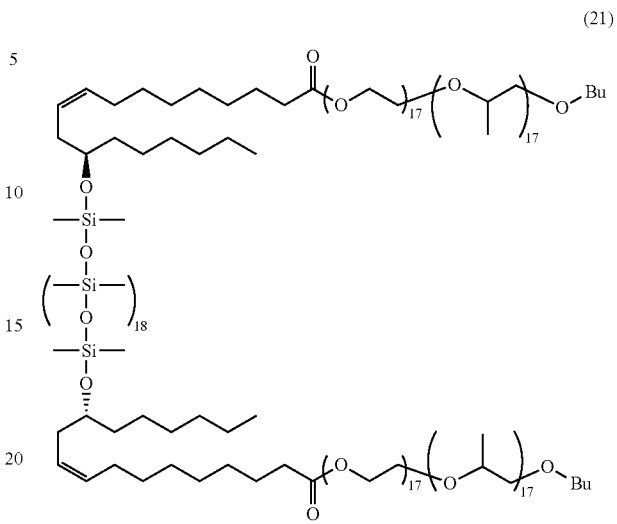

(21)

<Defoaming Agent Composition>
(A) Gemini-type Alkyl-polyoxyalkylene-modified Silicone
  (a-1): Composition (formula (11)) obtained in (IV) of working example 2
  (a-2): Composition (formula (21)) obtained in (XIV) of working example 7
  (a-3): Composition (formula (12)) obtained in (V) of working example 2
  (a-4): Composition (formula (9)) obtained in (II) of working example 1
(B) Silicone Oil Compound
  (b-1) Silicone Mixture 1
  A silicone compound was obtained by mixing, under a nitrogen gas atmosphere at 150° C. for 3 hours, 90 parts by mass of a dimethylpolysiloxane (by Shin-Etsu Chemical Co., Ltd.,
  KF96 (1,000 cs)) having a viscosity of 1,000 mm$^2$/s; and 10 parts by mass of a hydrophilic wet silica (by TOSOH SILICA CORPORATION, Nipsil HD-2, BET specific surface area: 300 m$^2$/g).
  (b-2) Silicone Mixture 2
  A dimethylpolysiloxane (by Shin-Etsu Chemical Co., Ltd., KF96 (1,000 cs)) of an amount of 90 parts by mass and having a viscosity of 1,000 mm$^2$/s; a hydrophobic fumed silica (by NIPPON AEROSIL Co., Ltd., Aerosil R974, BET specific surface area: 170 m$^2$/g) of an amount of 10 parts by mass; and a potassium siliconate (by Shin-Etsu Chemical Co., Ltd.) of an amount of 5 parts by mass and containing potassium hydroxide at a ratio of 3%, were mixed together under a nitrogen gas atmosphere at 150° C. for 3 hours, followed by neutralizing the same with 2-chloroethanol, and then eliminating the low-boiling fractions to eventually obtain a silicone oil compound.
(C) Polyoxyalkylene-modified Organopolysiloxane
  (c-1) Polyoxyalkylene-modified organopolysiloxane 1 having an average composition represented by the following general formula (22) and a viscosity of 1,720 mm$^2$/s

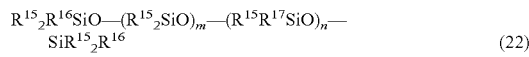
(22)

(In the above formula, $R^{15}$ and $R^{16}$ represent —$CH_3$; $R^{17}$ represents —$C_3H_6O(CH_2CH_2O)_{23}(CH_2CH(CH_3)O)_{23}C_4H_9$; m represents 27; and n represents 3.)

(c-2) Polyoxyalkylene-modified organopolysiloxane 2 having an average composition represented by the following formula (23) and a viscosity of 1,100 mm²/s $$R^{18}{}_2R^{20}SiO-(R^{19}{}_2SiO)_x-(R^{19}R^{20}SiO)_y-SiR^{18}{}_2R^{20} \quad (23)$$

(Here, $R^{18}$ represents $-CH_3$; $R^{20}$ represents $-C_3H_6O(C_2H_4O)_6(C_3H_6O)_{24}CH_3$; $R^{19}$ represents $-C_{13}H_{27}$; x represents 80; and y represents 2.)

(D) Polyoxyalkylene Polymer
(d-1) Polyoxyalkylene polymer having an average composition represented by the following formula (24)

$$CH_2=CHCH_2O-(C_2H_4O)_{21}(C_3H_6O)_{21}-CH_3 \quad (24)$$

(d-2) Polyoxyalkylene polymer having an average composition represented by the following formula (25)

$$HO-(C_2H_4O)_{25}(C_3H_6O)_{35}-H \quad (25)$$

<Preparation of Defoaming Agent Composition>

A defoaming agent composition was prepared by using a homomixer to mix a Gemini-type alkyl-polyoxyalkylene-modified silicone (A), a silicone oil compound (B), a polyoxyalkylene-modified organopolysiloxane (C) and a polyoxyalkylene polymer (D) of the amounts (part by mass) shown in Table 1. The defoaming performance, water dispersibility and product stability of such defoaming agent composition were then evaluated.

<Defoaming Performance Test>

An emulsion was prepared by using a spatula to stir together 1 g of the defoaming agent composition obtained in accordance with Table 1 and 1 g of an ion-exchange water. Next, 8 g of such ion-exchange water was further used to dilute the emulsion, thus obtaining a solution diluted by 10 times. As a foam liquid, 150 mL of a 0.2% by mass aqueous solution of "Mama Lemon," a household kitchen synthetic detergent (by Lion Corporation), was loaded into an automatic circulation-type defoaming tester (by TECLIS INSTRUMENTS), and circulation was then started at a foam liquid temperature of 25° C. and a foam liquid circulation flow rate of 500 mL/min. The diluted defoaming agent composition was added thereto once a foam volume had reached 100 mL. The foam volume was measured 1 minute after adding the diluted defoaming agent composition, 2 minutes after adding the diluted defoaming agent composition, 3 minutes after adding the diluted defoaming agent composition, and then 5 minutes after adding the diluted defoaming agent composition, for the purpose of evaluating the defoaming performance. The results thereof are shown in Table 2.

<Water Dispersibility Test>

Loaded into a 150 mL transparent glass bottle (wide-mouthed glass bottle PS-No. 12) were 5 g of the defoaming agent composition prepared in accordance with Table 1 and 95 g of an ion-exchange water. A shaking apparatus was further used to stir the same at 250 rpm for 1 min, and the condition of the defoaming agent composition immediately after stopping stirring was then visually observed to evaluate a water dispersibility using the following criteria. The results thereof are shown in Table 2.

○: Emulsification was confirmed with the defoaming agent composition being completely dispersed
Δ: Undispersed portions of the defoaming agent composition were confirmed, though emulsification was partially observed
x: Scums were confirmed as there existed a large portion of the defoaming agent composition that had failed to dissolve, though emulsification was partially observed <Dilution Stability Test>

An emulsion was prepared by using a spatula to stir together 10 g of the defoaming agent composition obtained in accordance with Table 1 and 10 g of an ion-exchange water. Next, 80 g of such ion-exchange water was further used to dilute the emulsion, thus obtaining a solution diluted by 10 times. The condition of the diluted defoaming agent composition after being stored at 25° C. for 1 day was visually observed, and the evaluation was then performed using the following criteria. The results thereof are shown in Table 2.

○: Neither separation between oil layer and water layer nor scums were confirmed
Δ: Concentration separation between oil layer and water layer was confirmed/Scums were not confirmed
x: Both separation between oil layer and water layer; and scums were confirmed

TABLE 1

| | (A) Gemini-type alkyl-polyoxyalkylene-modified organopolysiloxane | | | | (B) Silicone oil compound | | (C) Polyoxyalkylene-modified organopolysiloxane | | (D) Polyoxyalkylene polymer | |
|---|---|---|---|---|---|---|---|---|---|---|
| | a-1 | a-2 | a-3 | a-4 | b-1 | b-2 | c-1 | c-2 | d-1 | d-2 |
| Working example A | 50 | | | | 20 | 20 | | 10 | | |
| Working example B | | 50 | | | 20 | 20 | | 10 | | |
| Working example C | | | 50 | | 20 | 20 | | 10 | | |
| Working example D | | | | 50 | 20 | 20 | | 10 | | |
| Working example E | 45 | | | | 20 | 20 | | 10 | 5 | |
| Working example F | 45 | | | | 20 | 20 | | 10 | | 5 |
| Comparative example A | | | | | 20 | 20 | 50 | 10 | | |
| Comparative example B | 60 | | | | 20 | 20 | | | | |
| Comparative example C | 50 | | | | 5 | 5 | | 10 | | |

TABLE 2

| | Defoaming performance [mL] | | | | Water dispersibility | Dilution stability |
|---|---|---|---|---|---|---|
| | 1 minute later | 2 minutes later | 3 minutes later | 5 minutes later | | |
| Working example A | 0 | 21 | 58 | 162 | ○ | ○ |
| Working example B | 12 | 26 | 82 | 188 | ○ | ○ |

TABLE 2-continued

| | Defoaming performance [mL] | | | | Water dispersibility | Dilution stability |
| --- | --- | --- | --- | --- | --- | --- |
| | 1 minute later | 2 minutes later | 3 minutes later | 5 minutes later | | |
| Working example C | 5 | 37 | 90 | 165 | ○ | ○ |
| Working example D | 20 | 49 | 61 | 160 | ○ | ○ |
| Working example E | 5 | 25 | 78 | 170 | ○ | ○ |
| Working example F | 4 | 26 | 73 | 177 | ○ | ○ |
| Comparative example A | 22 | 91 | 179 | >200 | Δ | Δ |
| Comparative example B | | (Unmeasurable) | | | X | X |
| Comparative example C | 73 | >200 | — | — | ○ | ○ |

The invention claimed is:

1. A Gemini-type alkyl-polyoxyalkylene-modified silicone represented by formula (A):

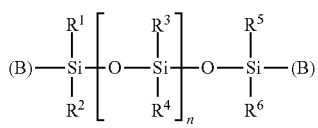

wherein $R^1$, $R^2$, $R^3$, $R^4$, $R^5$ and $R^6$ are identical to or different from one another, and each may have a halogen atom, a hydroxyl group, an amino group, a thiol group or a hydrosilyl group, representing: an alkyl group that has 1 to 30 carbon atoms; a cycloalkyl group that has 3 to 30 carbon atoms; an aryl group that has 6 to 30 carbon atoms; or an aralkyl group that has 7 to 30 carbon atoms, n represents an integer of 0 to 300, and (B) represents either an identical group or different groups expressed by formula (1):

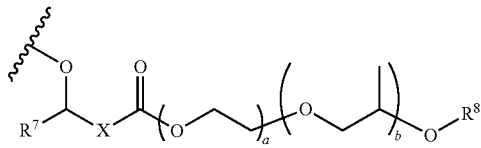

wherein each of $R^7$ and X represents a hydrocarbon group that has 1 to 40 carbon atoms and may be substituted by a halogen atom, an alkoxy group, a nitro group, a cyano group or a substituted amino group; $R^8$ represents a hydrogen atom, a hydrocarbon group having 1 to 30 carbon atoms, a formyl group or an acyl group having 2 to 30 carbon atoms; and a and b represent numbers satisfying $2 \leq a \leq 200$ and $0 \leq b \leq 200$, provided that $a+b=2$ to 200.

2. A method of producing a Gemini-type alkyl-polyoxyalkylene-modified silicone as set forth in claim 1, comprising:
   (1) condensing a mono-endcapped polyoxyalkylene and a hydroxyalkyl carboxylic acid derivative by either
   (a) a transesterification reaction between hydroxyl groups of said mono-endcapped polyoxyalkylene and hydroxyalkyl carboxylic acid ester, or
   (b) an esterification reaction between hydroxyl groups of said mono-endcapped polyoxyalkylene and carboxyl groups of hydroxyalkyl carboxylic acid; and
   (2) reacting a hydroxyalkyl-polyoxyalkylene condensate obtained in said (1) condensing and an organopolysiloxane having a reactive group at both terminals by either
   (c) a dehydrocondensation reaction between hydroxyl groups of said hydroxyalkyl-polyoxyalkylene condensate and an organopolysiloxane having a hydrosilyl group at both terminals in the presence of a platinum group metal catalyst or a base catalyst, or
   (d) a condensation reaction between hydroxyl groups of said hydroxyalkyl-polyoxyalkylene condensate and an organopolysiloxane having at both terminals a hydrolyzable group directly bonded to a silicon atom in the presence of a condensation catalyst.

3. The method of claim 2, wherein said hydroxyalkyl carboxylic acid derivative is at least one member selected from the group consisting of a ricinoleic acid, a 12-hydroxystearic acid, a methyl ester of said ricinoleic acid, a methyl ester of said 12-hydroxystearic acid, an ethylester of said ricinoleic acid, an ethylester of said 12-hydroxystearic acid, an n-propylester of said ricinoleic acid, an n-propylester of said 12-hydroxystearic acid, an i-propylester of said ricinoleic acid, an i-propylester of said 12-hydroxystearic acid, a butylester of said ricinoleic acid and a butylester of said 12-hydroxystearic acid.

4. A defoaming agent composition comprising:
   (A) a Gemini-type alkyl-polyoxyalkylene-modified silicone in an amount of 1 to 80% by mass and represented by formula (A)

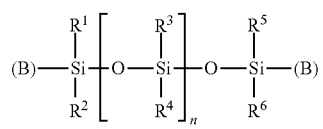

wherein $R^1$, $R^2$, $R^3$, $R^4$, $R^5$ and $R^6$ are identical to or different from one another, and each may have a halogen atom, a hydroxyl group, an amino group, a thiol group or a hydrosilyl group, representing: an alkyl group that has 1 to 30 carbon atoms; a cycloalkyl group that has 3 to 30 carbon atoms; an aryl group that has 6 to 30 carbon atoms; or an aralkyl group that has 7 to 30 carbon atoms, n represents an integer of 0 to 300, and (B) represents either an identical group or different groups expressed by formula (1):

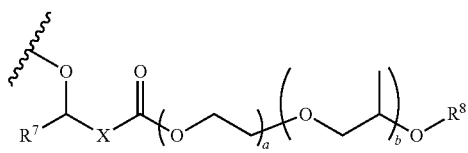

(1)

wherein each of $R^7$ and X represents a hydrocarbon group that has 1 to 40 carbon atoms and may be substituted by a halogen atom, an alkoxy group, a nitro group, a cyano group or a substituted amino group; $R^8$ represents a hydrogen atom, a hydrocarbon group having 1 to 30 carbon atoms, a formyl group or an acyl group having 2 to 30 carbon atoms;

and a and b represent numbers satisfying $2 \leq a \leq 200$ and $0 \leq b \leq 200$, provided that a+b=2 to 200;

(B) a silicone oil compound in an amount of 15 to 60% by mass and containing:

(a) an organopolysiloxane exhibiting a viscosity of 10 to 100,000 mm²/s at 25° C. and represented by formula (3)

(3)

wherein each $R^9$ independently represents a substituted or an unsubstituted monovalent hydrocarbon group; and c represents a number of 1.9 to 2.2; and (b) a finely powdered silica in an amount of 0.1 to 30 parts by mass with respect to 100 parts by mass of said component (a), and exhibiting a specific surface area not smaller than 100 m²/g by BET method; and (C) at least one kind of a polyoxyalkylene-modified organopolysiloxane in an amount of 5 to 95% by mass.

5. The defoaming agent composition according claim 4, further comprising (D) at least one kind of a polyoxyalkylene polymer in an amount of 5 to 80% by mass.

6. A method of producing a Gemini-type alkyl-polyoxyalkylene-modified silicone represented by formula (A):

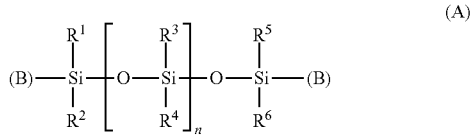

(A)

wherein $R^1$, $R^2$, $R^3$, $R^4$, $R^5$ and $R^6$ are identical to or different from one another, and each may have a halogen atom, a hydroxyl group, an amino group, a thiol group or a hydrosilyl group, representing: an alkyl group that has 1 to 30 carbon atoms; a cycloalkyl group that has 3 to 30 carbon atoms; an aryl group that has 6 to 30 carbon atoms; or an aralkyl group that has 7 to 30 carbon atoms, n represents an integer of 0 to 300, and (B) represents either an identical group or different groups expressed by formula (2):

(2)

wherein X represents a hydrocarbon group that has 1 to 40 carbon atoms and may be substituted by a halogen atom, an alkoxy group, a nitro group, a cyano group or substituted amino group; $R^8$ represents a hydrogen atom, a hydrocarbon group having 1 to 30 carbon atoms, a formyl group or an acyl group having 2 to 30 carbon atoms; and a and b represent numbers satisfying $2 \leq a \leq 200$ and $0 \leq b \leq 200$, provided that a+b=2 to 200, the method comprising:

(1) condensing a mono-endcapped polyoxyalkylene and a hydroxyalkyl carboxylic acid derivative by either (a) a transesterification reaction between hydroxyl groups of said mono-endcapped polyoxyalkylene and hydroxyalkyl carboxylic acid ester, or (b) an esterification reaction between hydroxyl groups of said mono-endcapped polyoxyalkylene and carboxyl groups of hydroxyalkyl carboxylic acid; and (2) reacting a hydroxyalkyl-polyoxyalkylene condensate obtained in said (1) condensing and an organopolysiloxane having a reactive group at both terminals by either (c) a dehydrocondensation reaction between hydroxyl groups of said hydroxyalkyl-polyoxyalkylene condensate and an organopolysiloxane having a hydrosilyl group at both terminals in the presence of a platinum group metal catalyst or a base catalyst, or (d) a condensation reaction between hydroxyl groups of said hydroxyalkyl-polyoxyalkylene condensate and an organopolysiloxane having at both terminals a hydrolyzable group directly bonded to a silicon atom in the presence of a condensation catalyst.

7. The method of claim 6, wherein said hydroxyalkyl carboxylic acid derivative is at least one member selected from the group consisting of a ricinoleic acid, a 12-hydroxystearic acid, a methyl ester of said ricinoleic acid, a methyl ester of said 12-hydroxystearic acid, an ethylester of said ricinoleic acid, an ethylester of said 12-hydroxystearic acid, an n-propylester of said ricinoleic acid, an n-propylester of said 12- hydroxystearic acid, an i-propylester of said ricinoleic acid, an i-propylester of said 12-hydroxystearic acid, a butylester of said ricinoleic acid and a butylester of said 12-hydroxystearic acid.

* * * * *